US011524948B2

(12) United States Patent
Jung et al.

(10) Patent No.: US 11,524,948 B2
(45) Date of Patent: Dec. 13, 2022

(54) PRODRUGS OF ALPHA-KETOGLUTARATE, ALPHA-KETOBUTYRATE, ALPHA-KETOISOVALERATE, AND ALPHA-KETOISOHEXANOATE, AND USES THEREOF

(71) Applicant: The Regents of the University of California, Oakland, CA (US)

(72) Inventors: Michael E. Jung, Los Angeles, CA (US); Jing Huang, Los Angeles, CA (US); Yanpeng Xing, Los Angeles, CA (US); Brett E. Lomenick, Los Angeles, CA (US); Min Chai, Los Angeles, CA (US); Xudong Fu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/916,845

(22) Filed: Jun. 30, 2020

(65) Prior Publication Data

US 2020/0325113 A1 Oct. 15, 2020

Related U.S. Application Data

(63) Continuation of application No. PCT/US2019/056768, filed on Oct. 17, 2019.

(60) Provisional application No. 62/746,912, filed on Oct. 17, 2018.

(51) Int. Cl.
| C07D 319/12 | (2006.01) |
| C07D 317/34 | (2006.01) |
| C07C 69/007 | (2006.01) |
| C07F 9/113 | (2006.01) |

(52) U.S. Cl.
CPC .......... *C07D 319/12* (2013.01); *C07C 69/007* (2013.01); *C07D 317/34* (2013.01); *C07F 9/113* (2013.01)

(58) Field of Classification Search
CPC .. C07D 265/32; C07D 317/32; C07D 317/34; C07D 319/12
See application file for complete search history.

(56) References Cited

U.S. PATENT DOCUMENTS

| 2015/0376159 A1 | 12/2015 | Sels et al. |
| 2016/0254334 A1 | 9/2016 | Yang et al. |
| 2016/0354334 A1 | 12/2016 | Huang et al. |

FOREIGN PATENT DOCUMENTS

| WO | WO-2006/066244 A2 | 6/2006 |
| WO | WO-2014/122294 A1 | 8/2014 |
| WO | WO-2015/123229 A1 | 8/2015 |
| WO | WO-2020/081836 A1 | 4/2020 |

OTHER PUBLICATIONS

Hedge et al. (J. Org. Chem. 1961, 26, 3166-3170).*
El-Newaihy MF (Australian Journal of Chemistry (1976) 29(1), 223-227).*
Fan (Tetrahedron (2006) 62(29), 6782-6791).*
Sep. 21, 2006 per STN/CAPLUS.*
Fan (Gaodeng Xuexiao Huaxue Xuebao (2013) 34(7), 1731-1738).*
Adlington et al. (Journal of the Chemical Society, Perkin Transactions 1: Organic and Bio-Organic Chemistry (1972-1999) (1981), (11), 2848-63).*
STN/CAPLUS RN: 1822579-92-9 (Dec. 4, 2015).*
STN/CAPLUS RN: 1820716-90-2 (Nov. 16, 2015).*
Manjunath et al. (Journal of Carbohydrate Chemistry (2007), 26(1), 17-25).*
Choi et al. (Journal of Medicinal Chemistry (2007), 50(15), 3465-3481).*

(Continued)

*Primary Examiner* — Valerie Rodriguez-Garcia
(74) *Attorney, Agent, or Firm* — Foley Hoag LLP; David P. Halstead; Lucas P. Watkins

(57) ABSTRACT

The present disclosure provides compounds of Formula (VIA), Formula (IIIA), Formula (IVA), and Formula (VA). The compounds are prodrugs of alpha-ketoglutarate, alpha-ketobutryrate, alpha-ketoisovalerate, and alpha-ketoisohexanoate, which are useful in treating or preventing age related diseases, disorders, or conditions.

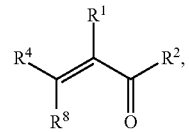

(VIA)

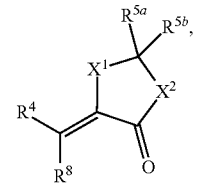

(IIIA)

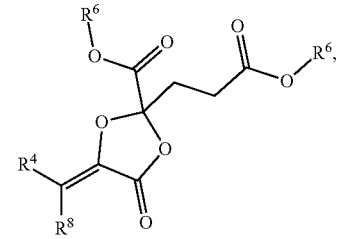

(IVA)

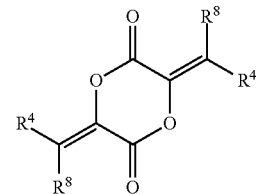

(VA)

12 Claims, 10 Drawing Sheets

(56) References Cited

OTHER PUBLICATIONS

Clennan, "Reactions of singlet oxygen with alkoxy-substituted dienes. Formation of dioxetanes in the singlet oxygenations of s-cis fixed dienes (Z,Z)-and (E, Z)-4, 5-diethylidene-2, 2-dimethyl-1, 3-dioxolanes," The Journal of Organic Chemistry, 52(2):294-296 (1987).

Dusselier et al., "Shape-selective zeolite catalysis for bioplastics production," Science, 349(6243):78-80 (2015).

Ghomri, "Synthesis of phosphoenol pyruvates. Theoretical and experimental study," Competes Rendus Chimie, 17(12):1230-1236 (2014).

International Search Report and Written Opinion for International Application No. PCT/US2019/056768 dated Dec. 31, 2019.

Mager, "Branching in structure-toxicity relationships applied to organophosphorus pesticides of the DDVP (dichlorvos) type: a novel phenomenon in QSAR," Pharmazie, 36(6):448-449 (1981).

Monnin, "Reactions of aliphatic amines with enol acetates and enol ethers of a-oxoacid esters," Helvetica Chimica Acta, 40:1983-1989 (1957).

Monnin, "Some enol acetates and enol ethers of pyruvic ester in the Diels-Alder reaction," Chimia, 11:337-338 (1957).

Seifert et al., "Some reactions with derivatives of α-keto acids and α-keto esters," Helvetica Chimica Acta, 33:725-736 (1950).

Zhang et al., "Chemical synthesis of functional poly(4-hydroxybutyrate) with controlled degradation via intramolecular cyclization," Macromolecules, 46(24): 9554-9562 (2013).

Extended European Search Report for EP Application No. 19873125.9 dated Jun. 10, 2022.

* cited by examiner

PRODRUGS OF ALPHA-KETOGLUTARATE, ALPHA-KETOBUTYRATE, ALPHA-KETOISOVALERATE, AND ALPHA-KETOISOHEXANOATE, AND USES THEREOF

CROSS-REFERENCE TO RELATED APPLICATIONS

This application is a continuation of International Application No. PCT/US2019/056768, filed on Oct. 17, 2019, which claims the benefit of U.S. Provisional Application No. 62/746,912, filed Oct. 17, 2018, the entire contents of each of which are incorporated by reference herein.

BACKGROUND

Certain naturally occurring small molecules increase the lifespan of certain species, e.g., *C. elegans*, by 50-70%. Related effects are seen in mammals. In particular α-ketoglutarate is such a life-extending molecule. Other similar molecules, for example, 2-hydroxyglutarate, also have such effects. Such molecules are disclosed in U.S. Patent Pub. No. 2016/0354334. These life-extending effects are believed to be mediated by inhibition of ATP synthase and mTOR signaling.

Metabolism and aging are intimately linked. Compared to ad libitum feeding, dietary restriction (DR) or caloric restriction (CR) consistently extends lifespan and delays age-related diseases in evolutionarily diverse organisms. Similar conditions of nutrient limitation and genetic or pharmacological perturbations of nutrient or energy metabolism also have longevity benefits. Several compounds that modulate aging have been identified.

SUMMARY OF THE INVENTION

In certain aspects, the present disclosure provides compounds of formula I, II, or VI, preferably formula I or II, and pharmaceutically acceptable salts thereof:

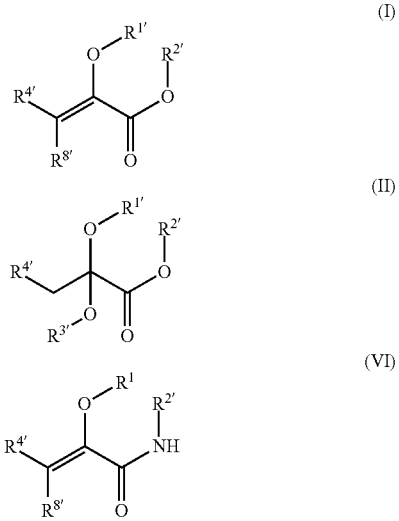

wherein:
$R^{1'}$ is acyl, preferably lower acyl, such as acetyl or propionyl, or $P(O)(OR^{7'})_2$;
$R^{2'}$ is alkyl, alkenyl or alkynyl, preferably lower alkyl; or $R^{1'}$ and $R^2$ taken together with the intervening atoms form a 5-7-membered ring;
$R^{3'}$ is alkyl, preferably lower alkyl; and
$R^{4'}$ is alkyl, preferably lower alkyl, most preferably methyl, or alkyloxycarbonylalkyl;
$R^{7'}$ is H, alkyl, or acyloxyalkyl;
$R^{8'}$ is H or alkyl, preferably H.

In certain embodiments, the compound is not

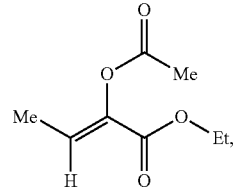

MJX001

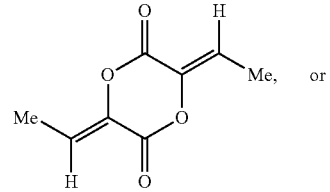

MJX004 or

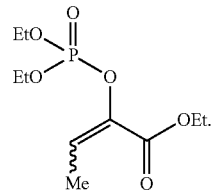

MJX007

In certain embodiments, $R^{1'}$ and $R^{2'}$ taken together form a five-membered ring, e.g., $R^{1'}$ and R taken together represent a substituted or unsubstituted methylene group. In certain such embodiments, the five-membered ring is substituted with one or two alkyl groups (i.e., the five-membered ring can be hydrolyzed to liberate an aldehyde or ketone). In other such embodiments, the methylene group is substituted by a) a carboxylate or an ester (e.g., a lower alkyl ester) of a carboxylate, and b) an alkyl group, i.e., the five-membered ring can be hydrolyzed to form compound 1 or an ester thereof and an alpha-ketoacid or (preferably) an alpha-ketoester. In certain such embodiments, the alpha-ketoacid/alpha-ketoester is compound 1 or an ester thereof (preferably a lower alkyl ester); in other such embodiments, the alpha-ketoacid/alpha-ketoester is compound 2 or an ester (e.g., a diester, preferably a lower alkyl diester) thereof.

In certain embodiments, $R^{1'}$ and $R^{2'}$ taken together form a six-membered ring. In certain such embodiments, the six-membered ring is symmetrical, i.e., the ring can be hydrolyzed to liberate two molecules of an alpha-ketoacid, such as compound 1. In other such embodiments, the ring is asymmetrical, i.e., the ring can be hydrolyzed to liberate two different alpha-ketoacids, such as compound 1 and compound 2.

In certain embodiments, $R^{1'}$ is acyl, such as acetyl; and $R^{2'}$ is alkyl, such as methyl or ethyl.

In certain embodiments, the compound is of formula (II) and $R^{3'}$ is alkyl, such as ethyl. In certain such embodiments, the compound is

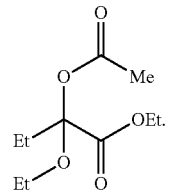

MJX002

In certain embodiments, the compound is of formula (I). In certain such embodiments, the compound is

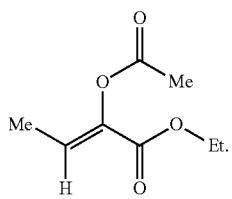

MJX001

In other such embodiments, the compound has a structure according to formula (Ia):

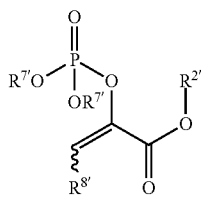

(Ia)

wherein $R^{2'}$ is alkyl; and $R^{7'}$ is alkyl, or acyloxyalkyl. In some such embodiments, $R^{7'}$ is acetoxymethyl or ethyl. In some such embodiments, the compound is

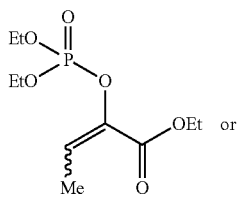

MJX007

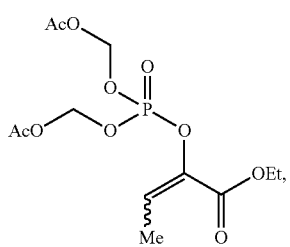

MJX009 such as MJX009.

In certain embodiments, the compound has a structure according to formula III:

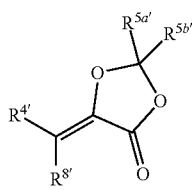

(III)

wherein $R^{5a'}$ is alkyl; and
$R^{5b'}$ is H, alkyl, or alkoxycarbonyl.

In certain such embodiments, $R^{5a'}$ is alkyl, such as methyl, and $R^{5b'}$ is H.

In other such embodiments, $R^{5a'}$ is alkyl (such as ethyl, isopropyl, or isobutyl), and $R^{5'}$ is alkoxycarbonyl, such as ethoxycarbonyl. In certain such embodiments, the compound has a structure according to formula IV:

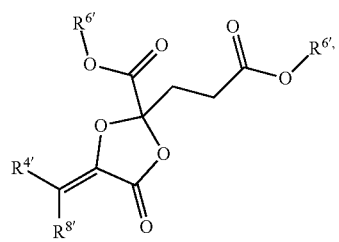

(IV)

wherein each $R^6$ is independently selected from alkyl.

In certain embodiments, the compound is

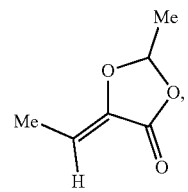

MJX003

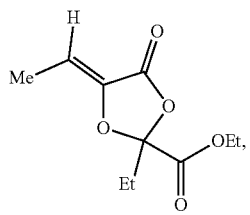

MJX005

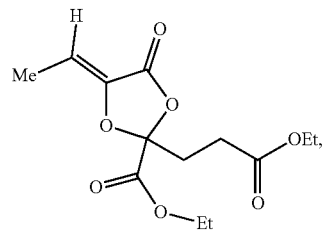

MJX006

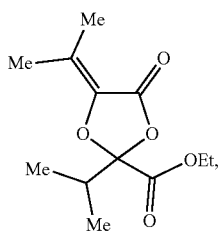

MJX008

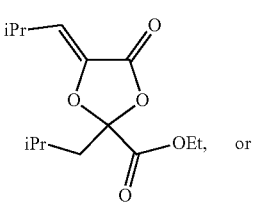

MJX010

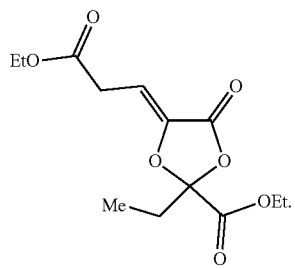

MJX012

In certain embodiments, the compound as a structure according to formula V:

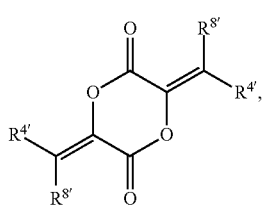

(V)

wherein each $R^4$ is independently selected from alkyl. In certain such embodiments, the compound is

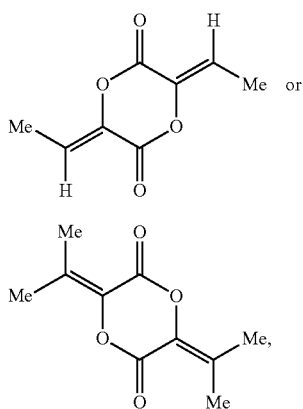

MJX004

MJX011 such as MJX011.

In certain embodiments, each $R^{4'}$ is independently selected from alkyl, such as methyl, ethyl, or isopropyl. In certain such embodiments, each $R^{4'}$ is methyl, ethyl, or isopropyl.

In certain embodiments, each $R^{8'}$ is hydrogen. In other embodiments, each $R^{8'}$ is methyl.

In certain aspects, the present invention is directed to a compound selected from:

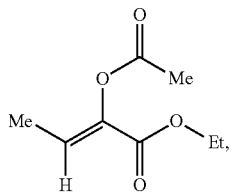

MJX001

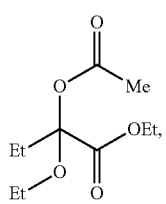

MJX002

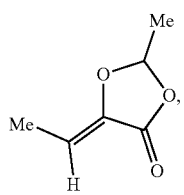

MJX003

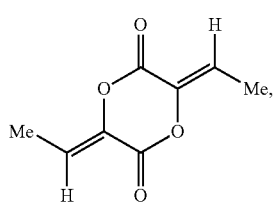

MJX004

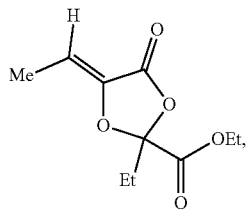

MJX005

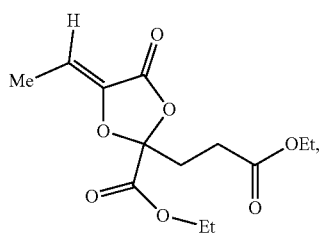

MJX006

MJX007

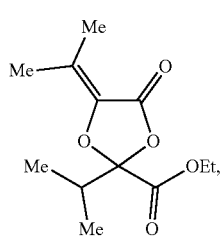

MJX008

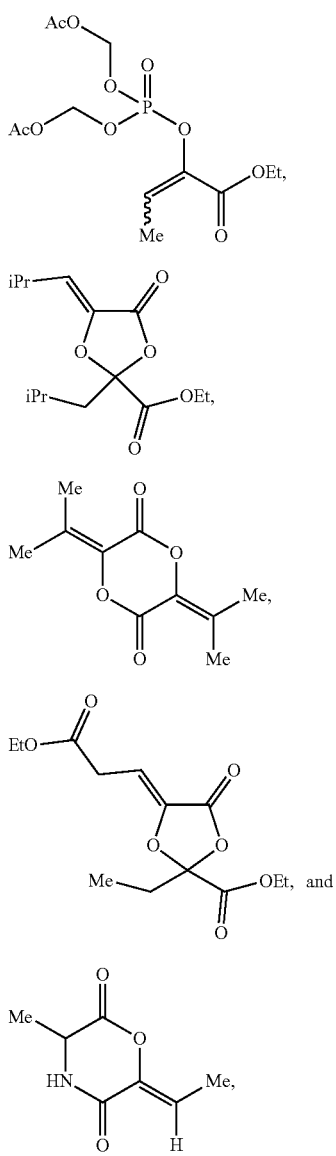

such as MJX002, MJX003, MJX005, MJX006, MJX008, MJX009, MJX010, MJX011, MJX012, or MJX013, or a pharmaceutically acceptable salt thereof. In certain embodiments, the compound is selected from MJX001, MJX002, MJX003, MJX004, MJX005, MJX006, MJX007, MJX008, MJX009, MJX010, MJX011, and MJX012, such as MJX002, MJX003, MJX005, MJX006, MJX008, MJX009, MJX010, MJX011, or MJX012, or a pharmaceutically acceptable salt thereof. In certain such embodiments, the compound is MJX007 or MJX009, such as MJX009. In other embodiments, the compound is MJX013.

In certain embodiments, the present invention is directed to a compound disclosed herein for use in treating or preventing aging or an aging-related disease or disorder, such as wherein the aging or aging-related disease or disorder is associated with increased activity of ATP synthase, mTOR signaling, or a combination thereof. In some such embodiments, the compound extends the lifespan of a mammal.

In certain aspects, the present disclosure provides a pharmaceutical composition comprising a compound as disclosed herein and a pharmaceutically acceptable excipient. In certain embodiments, the pharmaceutical composition is formulated for administration by intravenous administration, subcutaneous administration, oral administration, inhalation, nasal administration, transdermal administration, or ophthalmic administration. In certain embodiments, the pharmaceutical composition is in the form of a tablet, a pill, a capsule, a liquid, a suspension, a gel, a dispersion, a solution, an emulsion, an ointment, or a lotion.

In certain aspects, the present disclosure provides methods of slowing aging, extending lifespan, or treating an aging-related disease in a subject, comprising administering a compound or composition as disclosed herein.

DETAILED DESCRIPTION OF THE INVENTION

Figure 1A:
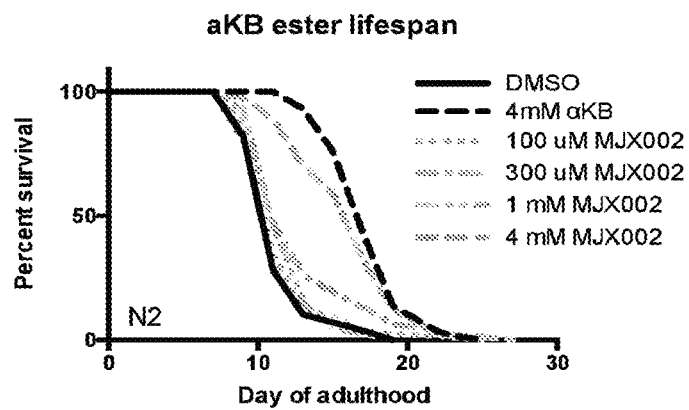
FIGS. 1A-1C show the effects of exemplary compounds of the present disclosure on the lifespan of C. elegans.

The present disclosure provides small molecule prodrugs that, upon administration, release life-extending molecules such as α-ketoglutarate or α-ketobutyrate. MJX001-MJX006, MJX007, MJX009, MJX012, and MJX013 are esters that, upon hydrolysis, release α-ketobutyric acid, the small molecule that increases life expectancy. MJX001-MJX005, MJX007, and MJX009 release only α-ketobutyric acid, while MJX006 and MJX012 each release both α-ketobutyrate and α-ketoglutarate, also a small molecule that increases life expectancy. MJX013 releases both α-ketobutyrate and alanine. MJX008 and MJX011 each release α-ketoisovalerate. MJX010 releases α-ketoisohexanoate.

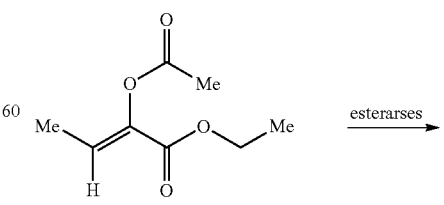

MJX001
Chemical Formula: $C_8H_{12}O_4$
Molecular Weight: 172.18

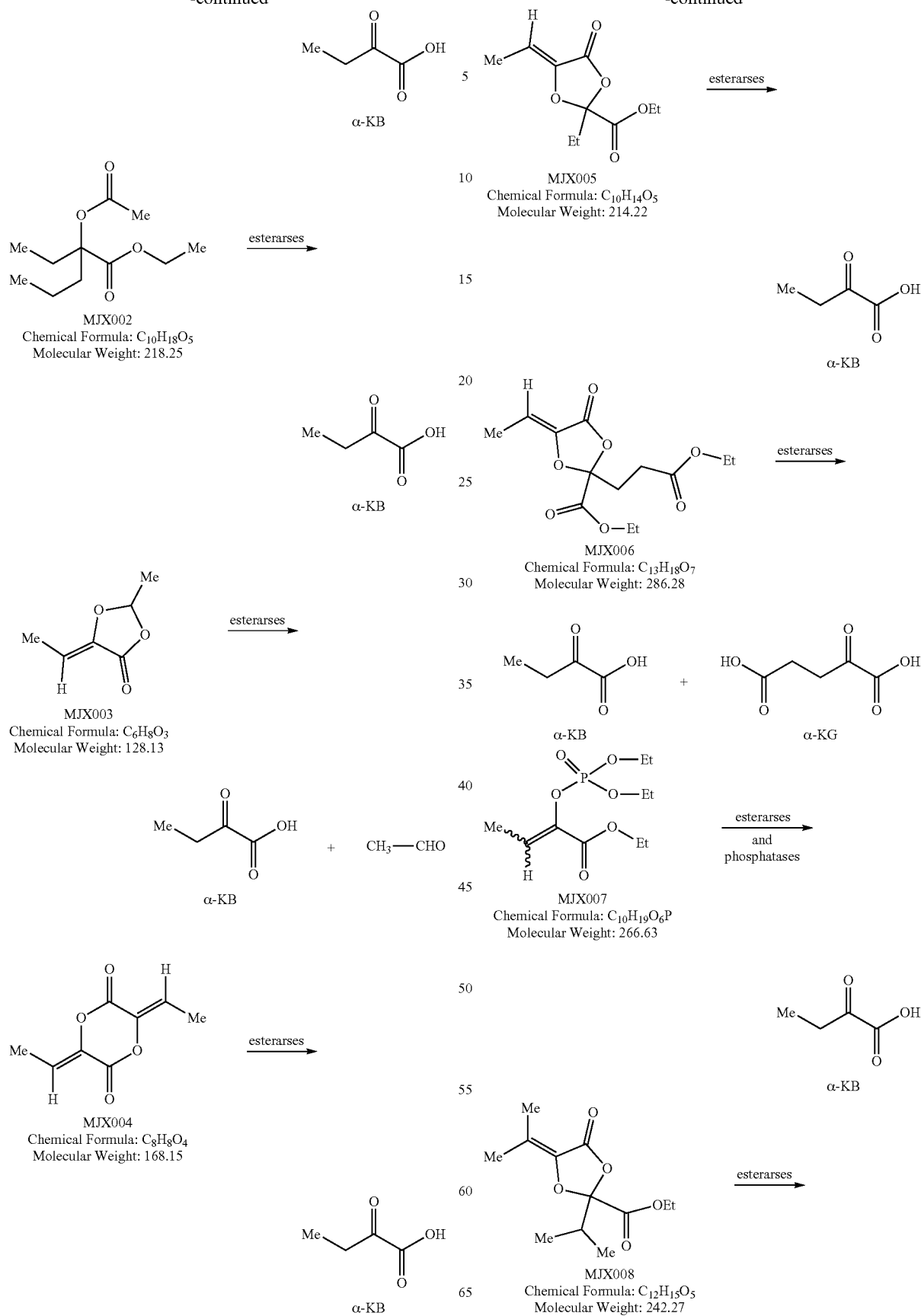

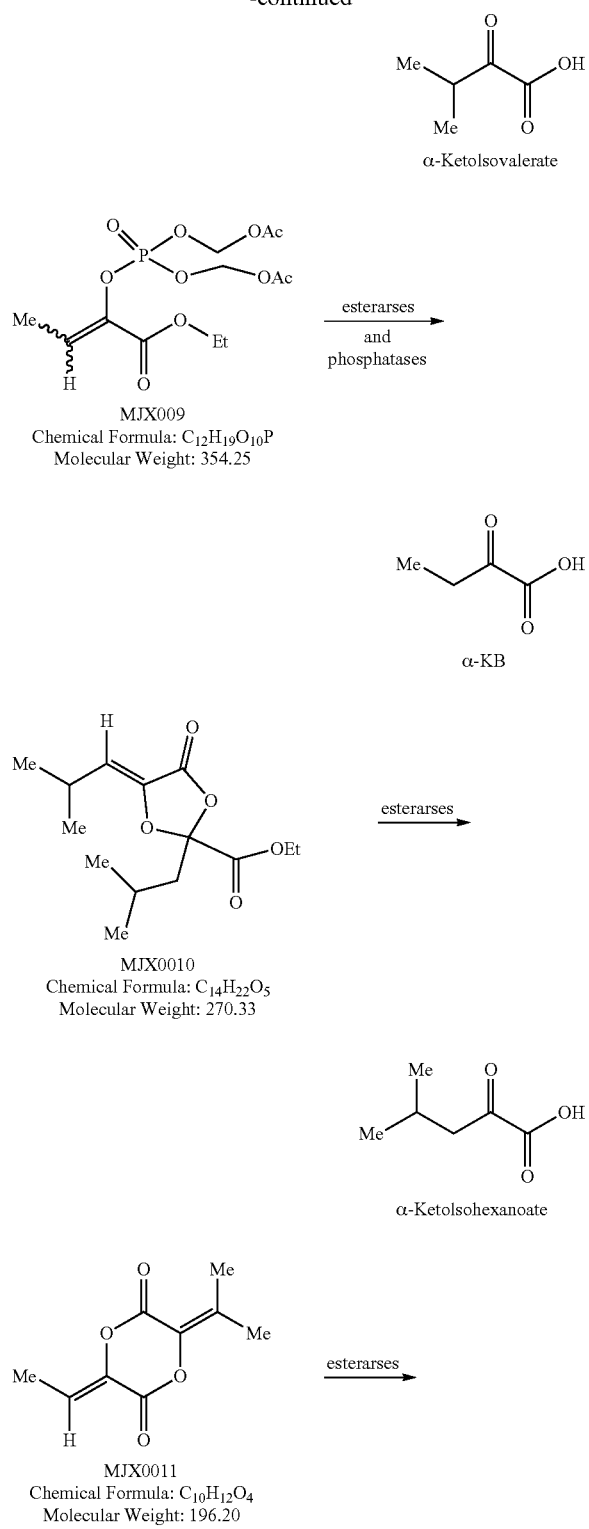
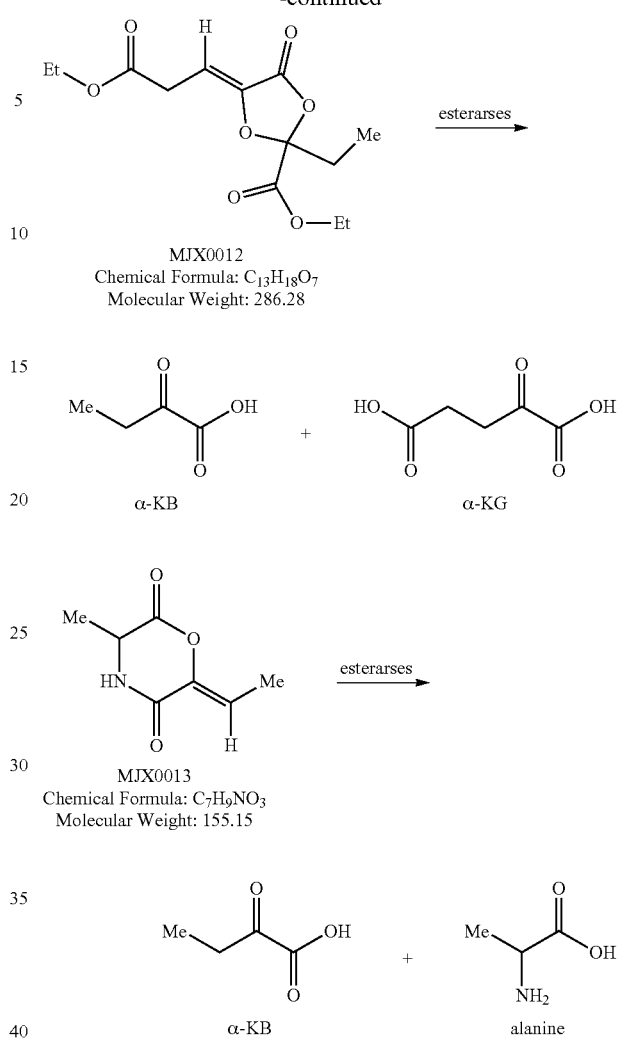

The compounds of the present disclosure are expected to react with non-specific esterases in cells to generate active life-extending molecules, such as α-ketobutyric acid (2-oxobutanoic acid). In addition, two compounds each generate one molecule of α-ketobutyric acid and a molecule of a second life-extending molecule, α-ketoglutaric acid. Compounds MJX001-MJX013 are shown below. For each compound, enzymatic, or non-enzymatic, hydrolysis of the esters and/or lactones present would generate the relevant active substance.

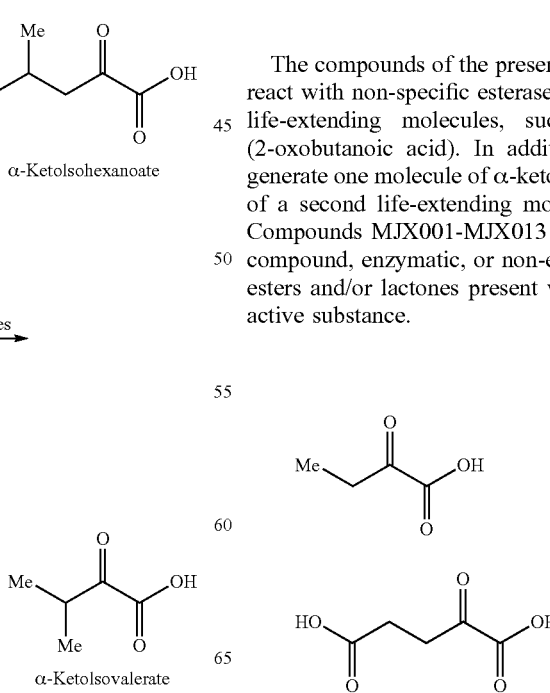

-continued

MJX001
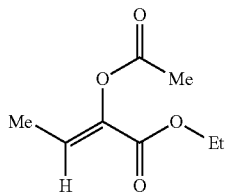

MJX002
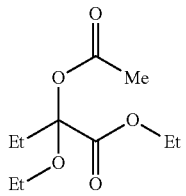

MJX003
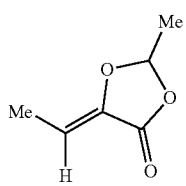

MJX004
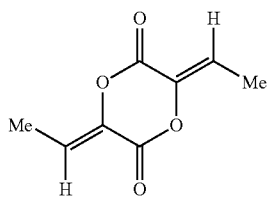

MJX005
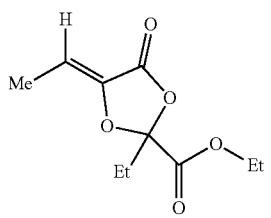

MJX006
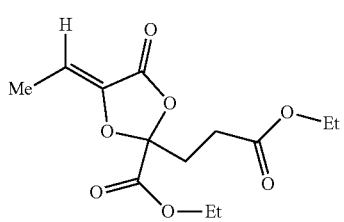

MJX007
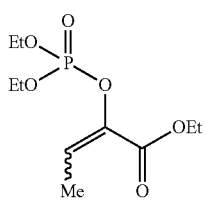

MJX008
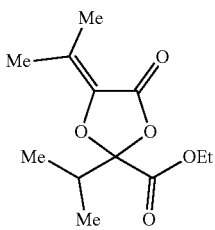

MJX009
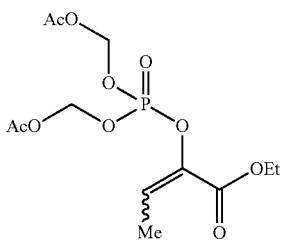

MJX010
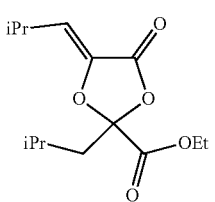

MJX011
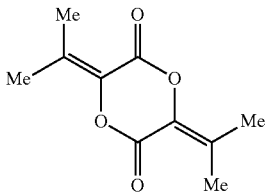

MJX012
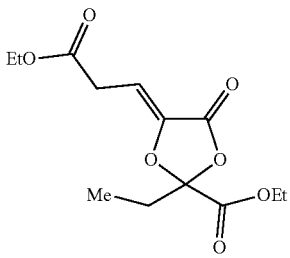

MJX013
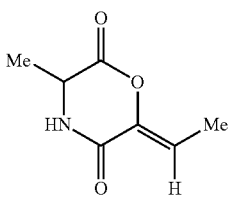

Certain embodiments provided herein describe methods for treating or inhibiting aging and age-related diseases in a subject which comprises administering to the subject at least one compound disclosed herein. In certain embodiments, the present disclosure is directed to methods for increasing the lifespan of a subject which comprises administering the subject at least one compound disclosed herein. Also provided herein in certain embodiments are compositions for treating or inhibiting aging and age-related diseases in a subject, said compositions comprise at least compound disclosed herein. In certain embodiments, provided herein are compositions for increasing the lifespan of a subject, said compositions comprising at compound disclosed herein. In certain embodiments, the subject is an animal, which may or may not be an animal model of aging or an age-related disease. In certain embodiments, the subject is a nematode, a rodent, or a non-human primate. In certain embodiments, the subject is a human.

In certain aspects, the present disclosure provides compounds of formula I, II, or VI, preferably formula I or II, and pharmaceutically acceptable salts thereof:

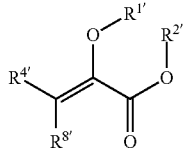
(I)

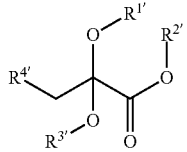
(II)

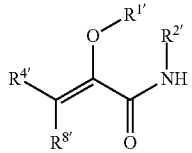
(VI)

wherein:
- $R^{1'}$ is acyl, preferably lower acyl, such as acetyl or propionyl, or $P(O)(OR^{7'})_2$;
- $R^{2'}$ is alkyl, alkenyl or alkynyl, preferably lower alkyl; or $R^{1'}$ and $R^{2'}$ taken together with the intervening atoms form a 5-7-membered ring;
- $R^{3'}$ is alkyl, preferably lower alkyl; and
- $R^{4'}$ is alkyl, preferably lower alkyl, most preferably methyl, or alkyloxycarbonylalkyl;
- $R^{7'}$ is H, alkyl, or acyloxyalkyl;
- $R^{8'}$ is H or alkyl, preferably H.

In certain embodiments, the compound is not

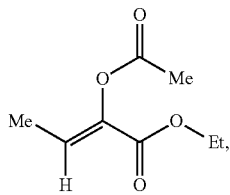
MJX001

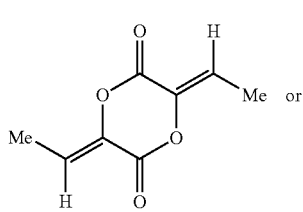
MJX004

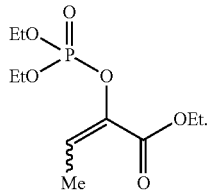
MJX007

In certain embodiments, $R^{1'}$ is acyl, such as acetyl; and $R^{2'}$ is alkyl, such as methyl or ethyl.

In certain embodiments, the compound is of formula (II) and $R^{3'}$ is alkyl, such as ethyl. In certain such embodiments, the compound is

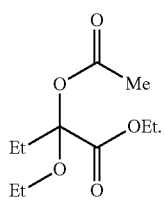
MJX002

In certain embodiments, the compound is of formula (I). In certain such embodiments, the compound is

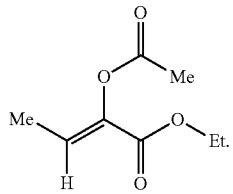
MJX001

In other such embodiments, the compound has a structure according to formula (Ia):

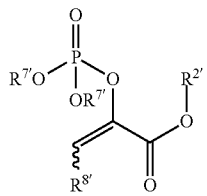
(Ia)

wherein $R^{2'}$ is alkyl; and $R^{7'}$ is alkyl, or acyloxyalkyl. In some such embodiments, $R^{7'}$ is acetoxymethyl or ethyl. In some such embodiments, the compound is

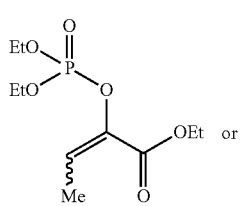
MJX007 or such as MJX009.

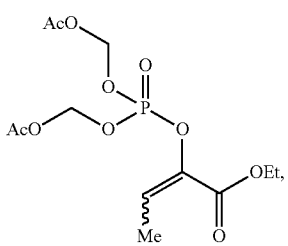
MJX009

In certain embodiments, the compound has a structure according to formula III:

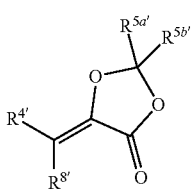
(III)

wherein $R^{5a'}$ is alkyl; and
$R^{5b'}$ is H, alkyl, or alkoxycarbonyl.

In certain such embodiments, $R^{5a'}$ is alkyl, such as methyl, and $R^{5b'}$ is H.

In other such embodiments, $R^{5a'}$ is alkyl (such as ethyl, isopropyl, or isobutyl), and $R^{5b'}$ is alkoxycarbonyl, such as ethoxycarbonyl. In certain such embodiments, the compound has a structure according to formula IV:

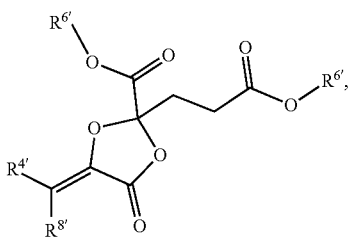
(IV)

wherein each $R^{6'}$ is independently selected from alkyl.

In certain embodiments, the compound is

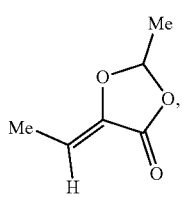
MJX003

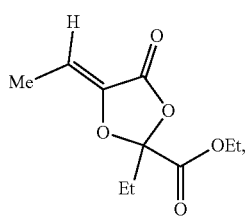
MJX005

MJX006

MJX008

MJX010

MJX012

In certain embodiments, the compound as a structure according to formula V:

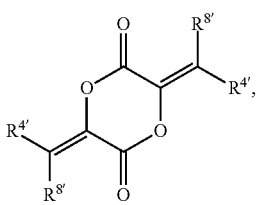
(V)

wherein each $R^{4'}$ is independently selected from alkyl. In certain such embodiments, the compound is

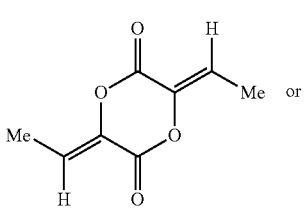
MJX004

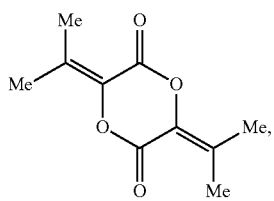
MJX011 such as MJX011.

In certain embodiments, each $R^{4'}$ is independently selected from alkyl, such as methyl, ethyl, or isopropyl. In certain such embodiments, each $R^{4'}$ is methyl, ethyl, or isopropyl.

In certain embodiments, each $R^{8'}$ is hydrogen. In other embodiments, each $R^{8'}$ is methyl.

In certain aspects, the present invention is directed to a compound selected from:

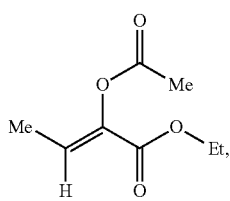
(MJX001)

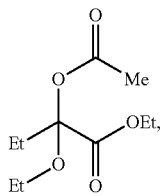
(MJX002)

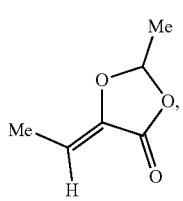
(MJX003)

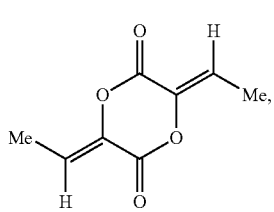
(MJX004)

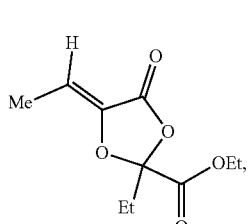
(MJX005)

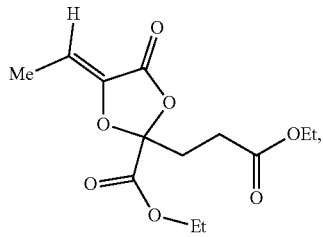
(MJX006)

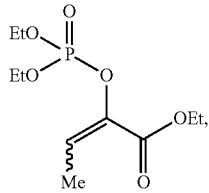
(MJX007)

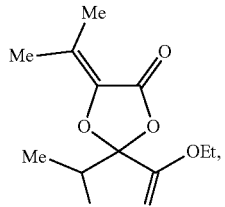
(MJX008)

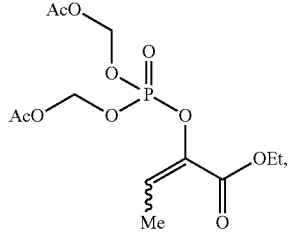
(MJX009)

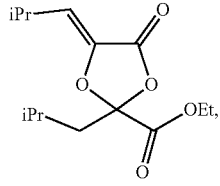
(MJX010)

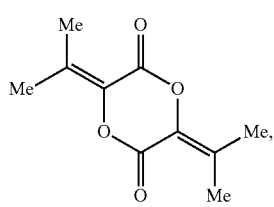
(MJX011)

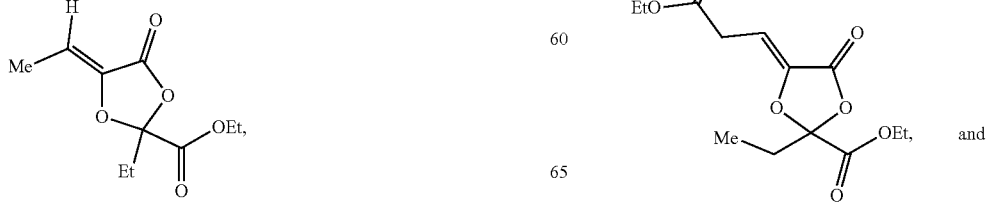
(MJX012)

and

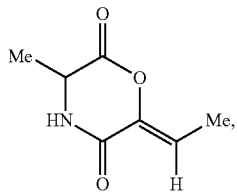

(MJX013)

such as MJX002, MJX003, MJX005, MJX006, MJX008, MJX009, MJX010, MJX011, MJX012, or MJX013, or a pharmaceutically acceptable salt thereof. In certain embodiments, the compound is selected from MJX001, MJX002, MJX003, MJX004, MJX005, MJX006, MJX007, MJX008, MJX009, MJX010, MJX011, and MJX012, such as MJX002, MJX003, MJX005, MJX006, MJX008, MJX009, MJX010, MJX011, or MJX012, or a pharmaceutically acceptable salt thereof. In certain such embodiments, the compound is MJX007 or MJX009, such as MJX009. In other embodiments, the compound is MJX013.

In certain embodiments, the present invention is directed to a compound disclosed herein for use in treating or preventing aging or an aging-related disease or disorder, such as wherein the aging or aging-related disease or disorder is associated with increased activity of ATP synthase, mTOR signaling, or a combination thereof. In some such embodiments, the compound extends the lifespan of a mammal.

In certain aspects, the present disclosure provides a pharmaceutical composition comprising a compound as disclosed herein and a pharmaceutically acceptable excipient. In certain embodiments, the pharmaceutical composition is formulated for administration by intravenous administration, subcutaneous administration, oral administration, inhalation, nasal administration, transdermal administration, or ophthalmic administration. In certain embodiments, the pharmaceutical composition is in the form of a tablet, a pill, a capsule, a liquid, a suspension, a gel, a dispersion, a solution, an emulsion, an ointment, or a lotion.

In certain aspects, the present disclosure provides methods of slowing aging, extending lifespan, or treating an aging-related disease in a subject, comprising administering a compound or composition as disclosed herein.

Compounds described herein, including salts and active metabolites thereof, are inhibitors of ATP synthase, mTOR signaling, or a combination thereof.

In certain aspects, the present disclosure provides compounds of formula I or II, and pharmaceutically acceptable salts thereof:

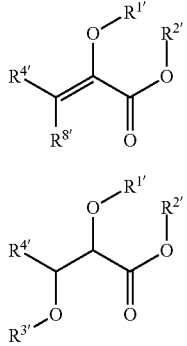

wherein:
R$^{1'}$ is acyl, preferably lower acyl, such as acetyl or propionyl, or P(O)(OR$^{7'}$)$_2$;
R$^{2'}$ is alkyl, alkenyl or alkynyl, preferably lower alkyl; or R$^{1'}$ and R$^{2'}$ taken together with the intervening atoms form a 5-7-membered ring;
R$^{3'}$ is alkyl, preferably lower alkyl; and
R$^{4'}$ is alkyl, preferably lower alkyl, most preferably methyl, or alkyloxycarbonylalkyl;
R$^{7'}$ is H, alkyl, or acyloxyalkyl;
R$^{8'}$ is H or alkyl, preferably H.

In some embodiments, R$^{1'}$ is acyl, such as acetyl; and R$^{2'}$ is alkyl, such as methyl or ethyl.

In some embodiments, the compound is of formula (II) and R$^{3'}$ is alkyl, such as ethyl. In some embodiments, the compound is MJX002. In some embodiments, the compound is of formula (I). In some embodiments, the compound is MJX001.

In certain embodiments, R$^{1'}$ and R$^{2'}$ taken together form a five-membered ring, e.g., R$^{1}$ and R$^{2'}$ taken together represent a substituted or unsubstituted methylene group. In certain such embodiments, the five-membered ring is substituted with one or two alkyl groups (i.e., the five-membered ring can be hydrolyzed to liberate an aldehyde or ketone). In other such embodiments, the methylene group is substituted by a) a carboxylate or an ester (e.g., a lower alkyl ester) of a carboxylate, and b) an alkyl group, i.e., the five-membered ring can be hydrolyzed to form α-ketobutyrate or an ester thereof and an alpha-ketoacid or (preferably) an alpha-ketoester. In certain such embodiments, the alpha-ketoacid/alpha-ketoester is α-ketobutyrate or an ester thereof (preferably a lower alkyl ester); in other such embodiments, the alpha-ketoacid/alpha-ketoester is α-ketoglutarate or an ester (e.g., a diester, preferably a lower alkyl diester) thereof.

In certain embodiments, R$^{1'}$ and R$^{2'}$ taken together form a six-membered ring. In certain such embodiments, the six-membered ring is symmetrical, i.e., the ring can be hydrolyzed to liberate two molecules of an alpha-ketoacid, such as α-ketobutyrate. In other such embodiments, the ring is asymmetrical, i.e., the ring can be hydrolyzed to liberate two different alpha-ketoacids, such as α-ketobutyrate and α-ketoglutarate.

In some embodiments, the compound has a structure according to formula (Ia):

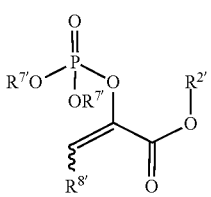

wherein R$^{2'}$ is alkyl; and
R$^{7'}$ is alkyl, or acyloxyalkyl.

In some embodiments, R$^{7'}$ is acetoxymethyl or ethyl. In some embodiments, the compound is MJX007 or MJX009.

In some embodiments, the compound has a structure according to formula (III):

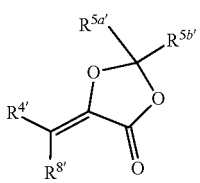

wherein $R^{5a'}$ is alkyl; and
$R^{5b'}$ is H, alkyl, or alkoxycarbonyl.

In some embodiments, $R^{5a'}$ is alkyl, such as methyl, and $R^{5b'}$ is H. In some embodiments, $R^{5a'}$ is alkyl (such as ethyl, isopropyl, or isobutyl), and $R^{5b'}$ is alkoxycarbonyl, such as ethoxycarbonyl.

In some embodiments, the compound has a structure according to formula (IV):

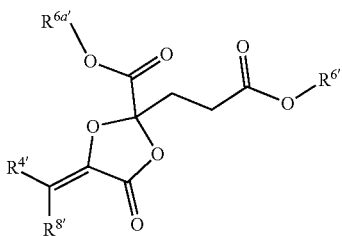

wherein each $R^{6'}$ is independently selected from alkyl.

In some embodiments, the compound is MJX003, MJX005, MJX006, MJX008, MJX010, or MJX012.

In some embodiments, the compound has a structure according to formula (V):

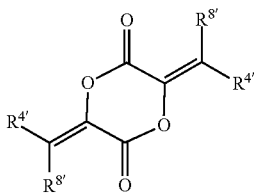

wherein each $R^{4'}$ is independently selected from alkyl.

In some embodiments, the compound is MJX004 or MJX011. In some embodiments, each $R^{4'}$ is independently selected from alkyl (such as methyl, ethyl, or isopropyl). In some embodiments, each $R^{4'}$ is methyl, ethyl, or isopropyl. In some embodiments, each $R^{8'}$ is hydrogen. In some embodiments, each $R^{8'}$ is methyl.

In one aspect, the disclosure provides a compound of Formula IA, or a pharmaceutically acceptable salt thereof:

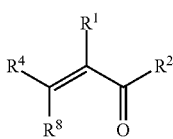

wherein:
$R^1$ is —O(C=O)(alkyl) or —OP(=O)(OR$^7$)$_2$;
$R^2$ is —OH, unsubstituted or substituted haloalkyl, unsubstituted or substituted alkyl, unsubstituted or substituted alkyne, unsubstituted or substituted alkene, unsubstituted or substituted alkoxy, unsubstituted or substituted alkenoxy, or unsubstituted or substituted alkynoxy, or unsubstituted or substituted heteroalkyl; or $R^1$ and $R^2$ are taken together with the intervening atoms to form a fused 5-, 6-, or 7-membered ring containing 0-3 N atoms and 0-3 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO$_2$(alkyl);

$R^4$ is unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;

$R^7$ is H, unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne, or -(alkyl)O(C=O)(alkyl); and $R^8$ is H, halo, unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne.

In some embodiments, $R^1$ is —OP(=O)(O(alkyl)O(C=O)(alkyl)$_2$. In some embodiments, $R^1$ and $R^2$ are taken together with the intervening atoms to form a fused 5-, 6-, or 7-membered ring containing 0-3 N atoms and 0-3 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO$_2$(alkyl). In some embodiments, the intervening atoms to form a fused 5-, 6-, or 7-membered ring containing 0 N atoms and 2 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO$_2$(alkyl). In some embodiments, the intervening atoms form a fused 5-, 6-, or 7-membered ring containing 1 N atom and 1 O atom in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO$_2$(alkyl).

In some embodiments, the compound has the structure of Formula (IAA'), or a pharmaceutically acceptable salt thereof:

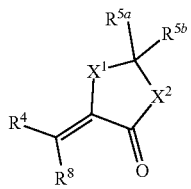

(IAA')

wherein:
X$^1$ and X$^2$ are independently OR$^9$, NR$^{10}$, or O;
R$^4$ is unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;
R$^{5a}$ is oxo, alkyl, or —CO$_2$(alkyl);
R$^{5b}$ is alkyl or -(alkyl)O(C=O)(alkyl);
R$^8$ is H, halo, unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;
R$^9$ is alkylene substituted with unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;
R$^{10}$ is H or unsubstituted or substituted alkyl; and
provided that when R$^{5a}$ is oxo, R$^{51}$ is absent.

In another aspect, the disclosure provides a compound for use in treating or preventing aging or an aging-related disease or disorder, wherein the compound has the structure of Formula IIA, or a pharmaceutically acceptable salt thereof:

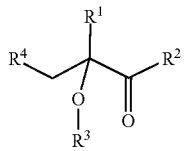

(IIA)

wherein:
R$^1$ is —O(C=O)(alkyl);
R$^2$ is alkoxy; or
R$^1$ and R$^2$ are taken together with the intervening atoms to form a fused 5-, 6-, or 7-membered ring containing 0-3 N atoms and 0-3 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO$_2$(alkyl);

R$^3$ is unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne; and R$^4$ is unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne.

In some embodiments, R$^4$ is unsubstituted or substituted alkyl. In some embodiments, R$^4$ is independently methyl, ethyl, or isopropyl. In some embodiments, R$^3$ is unsubstituted or substituted alkyl. In some embodiments, $^3$ is methyl, ethyl, propyl, or isopropyl.

In some embodiments, the compound is selected from:

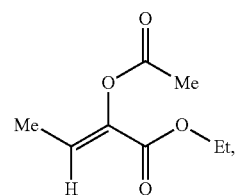

(MJX001)

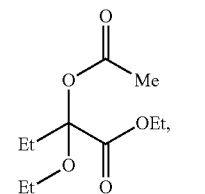

(MJX002)

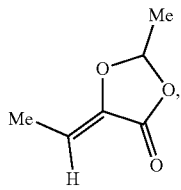

(MJX003)

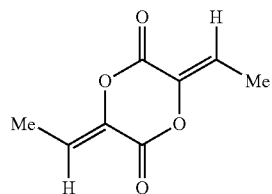

(MJX004)

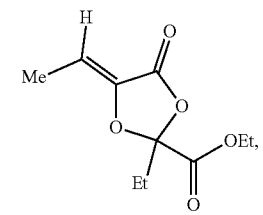

(MJX005)

-continued (MJX006) 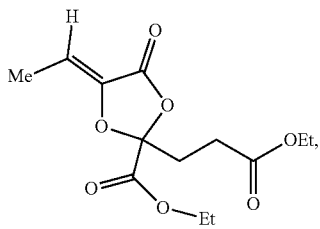

(MJX007) 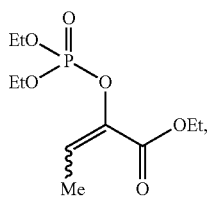

(MJX008) 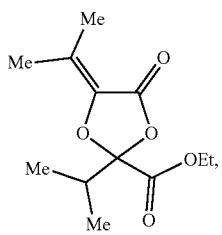

(MJX009) 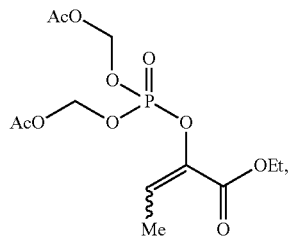

(MJX010) 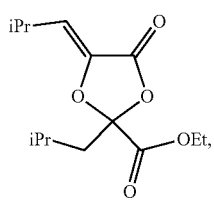

(MJX011) 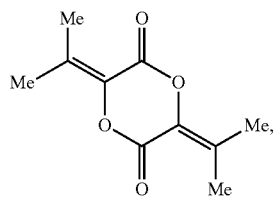

(MJX012) 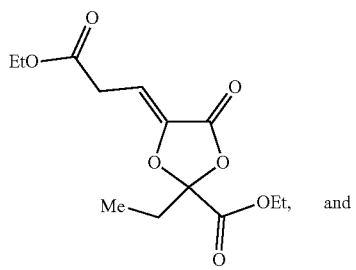 and (MJX013) 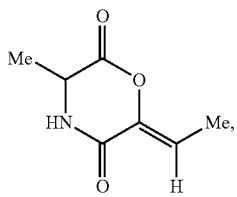

or a pharmaceutically acceptable salt thereof.

In some embodiments, the aging or aging-related disease or disorder is associated with increased activity of ATP synthase, mTOR signaling, or a combination thereof.

In some embodiments, the compounds described herein extend the lifespan of a mammal.

In another aspect, the disclosure provides a compound of Formula VIA, or a pharmaceutically acceptable salt thereof:

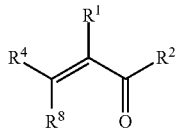

(VIA)

wherein:

$R^1$ is —OP(=O)(OR$^7$)$_2$;

$R^2$ is unsubstituted or substituted alkoxy, unsubstituted or substituted alkenoxy, or unsubstituted or substituted alkynoxy; or $R^1$ and $R^2$ are taken together with the intervening atoms to form a fused 5-, 6-, or 7-membered ring containing 0-2 N atoms and 1-3 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO$_2$(alkyl);

$R^4$ is unsubstituted or substituted alkyl;

$R^7$ is unsubstituted or substituted heteroalkyl, unsubstituted or substituted alkoxy, unsubstituted or substituted haloalkyl, unsubstituted or substituted alkene, or unsubstituted or substituted alkyne, or -(alkyl)O(C=O)(alkyl);

$R^8$ is H, unsubstituted or substituted alkyl; and provided that when the fused 5-, 6-, or 7-membered ring contains 1 O atom, the fused 5-, 6-, or 7-membered ring contains at least 1 N atom.

In some embodiments, the compound has the structure of Formula (IAA), or a pharmaceutically acceptable salt thereof:

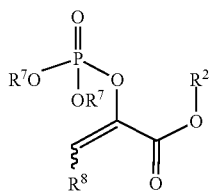

(IAA)

wherein:
R² is alkyl;
each R⁷ is -(alkyl)O(C=O)(alkyl); and
R is H or alkyl.

In some embodiments, the compound has the structure of Formula (IIIA), or a pharmaceutically acceptable salt thereof:

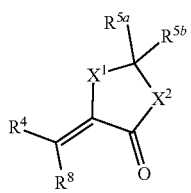

(IIIA)

wherein:
X¹ and X² are independently OR⁹, NR¹⁰, or O;
R⁴ is unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;
R⁵ᵃ is oxo, alkyl, or —CO₂(alkyl);
R⁵ᵇ is alkyl or -(alkyl)O(C=O)(alkyl);
R⁸ is H, halo, unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;
R⁹ is alkylene substituted with unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne;
R¹⁰ is H or unsubstituted or substituted alkyl;
provided that when R⁵ᵃ is oxo, R⁵ᵇ is absent; and
provided that when R⁵ᵃ or R⁵ᵇ is alkyl, the other of R⁵ᵃ or R⁵ᵇ is not alkyl.

In some embodiments, X¹ and X² are each O. In some embodiments, X¹ is N and X² is O. In some embodiments, X¹ is O and X² is N. In some embodiments, X¹ is OR⁹ and X² is O. In some embodiments, X¹ is O and X² is OR⁹. In some embodiments, X¹ is N and X² is N. In some embodiments, X¹ is N and X² is N.

In some embodiments, each X is O. In some embodiments, R⁵ᵃ is unsubstituted or substituted alkyl and R⁵ᵇ is H. In some embodiments, R⁵ᵃ is unsubstituted or substituted alkyl and R⁵ᵇ is -(alkyl)O(C=O)(alkyl).

In some embodiments, the compound has the structure of Formula (IVA), or a pharmaceutically acceptable salt thereof:

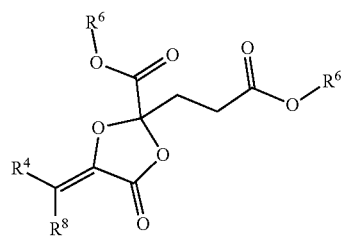

(IVA)

wherein
each R⁶ is alkyl;
R⁴ is unsubstituted or substituted alkyl; and
R⁸ is H, unsubstituted or substituted alkyl.

In some embodiments, the compound has the structure of Formula (VA), or a pharmaceutically acceptable salt thereof:

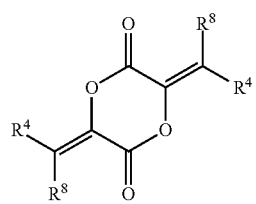

(VA)

wherein R⁴ and R⁸ are unsubstituted or substituted alkyl.

In an aspect, the disclosure provides a compound of formula VIIA, or a pharmaceutically acceptable salt thereof:

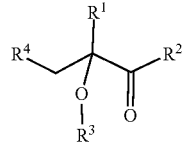

(VIIA)

wherein:
R¹ is —O(C=O)(alkyl);
R² is alkoxy; or
R¹ and 2 are taken together with the intervening atoms to form a fused 5-, 6-, or 7-membered ring containing 0-3 N atoms and 0-3 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —CO₂(alkyl);
R³ is unsubstituted or substituted alkyl, unsubstituted or substituted heteroalkyl, unsubstituted or substituted alkoxy, or unsubstituted or substituted alkene; and
R⁴ is unsubstituted or substituted alkyl, unsubstituted or substituted heteroalkyl, unsubstituted or substituted alkoxy, unsubstituted or substituted haloalkyl, unsubstituted or substituted alkene, or unsubstituted or substituted alkyne.

In some embodiments, $R^4$ is unsubstituted or substituted alkyl. In some embodiments, $R^4$ is independently methyl, ethyl, or isopropyl. In some embodiments, $R^3$ is unsubstituted or substituted alkyl. In some embodiments, $R^3$ is methyl, ethyl, propyl, or isopropyl.

In some embodiments, $R^1$ is —O(C=O)(methyl). In some embodiments, $R^1$ is —O(C=O)(ethyl). In some embodiments, $R^1$ is —O(C=O)(propyl). In some embodiments, $R^1$ is —O(C=O)(isopropyl). In some embodiments, $R^1$ is —O(C=O)(butyl). In some embodiments, $R^1$ is —OP(=O)(O(alkyl)O(C=O)(alkyl)$_2$. In some embodiments, $R^1$ is —OP(=O)(O(ethyl)O(C=O)(ethyl)$_2$.

In some embodiments, $R^2$ is unsubstituted or substituted alkoxy, unsubstituted or substituted alkenoxy, or unsubstituted or substituted alkynoxy, or unsubstituted or substituted heteroalkyl. In some embodiments, $R^3$ is unsubstituted or substituted alkoxy. In some embodiments, $R^2$ is methoxy. In some embodiments, 2 is ethoxy. In some embodiments, $R^2$ is propoxy.

In some embodiments, $R^8$ is H, unsubstituted or substituted alkyl, unsubstituted or substituted heteroalkyl, unsubstituted or substituted alkoxy, or unsubstituted or substituted haloalkyl. In some embodiments, $R^8$ is H or unsubstituted or substituted alkyl. In some embodiments, $R^8$ is H. In some embodiments, $R^8$ is unsubstituted or substituted alkyl. In some embodiments, $R^8$ is methyl. In some embodiments, $R^8$ is unsubstituted or substituted alkyl. In some embodiments, $R^8$ is ethyl. In some embodiments, $R^8$ is unsubstituted or substituted alkyl. In some embodiments, $R^8$ is propyl. In some embodiments, $R^8$ is unsubstituted or substituted alkyl. In some embodiments, $R^8$ is isopropyl. In some embodiments, $R^8$ is unsubstituted or substituted alkyl. In some embodiments, R is butyl.

In one aspect, the disclosure provides a compound selected from:

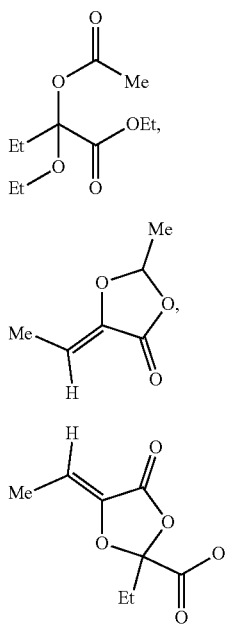

(MJX002)

(MJX003)

(MJX005)

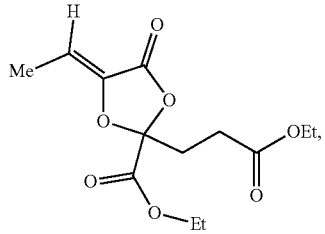

(MJX006)

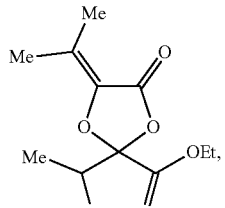

(MJX008)

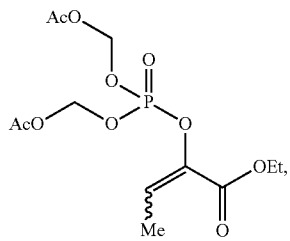

(MJX009)

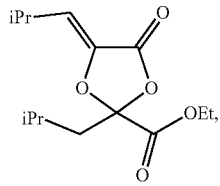

(MJX010)

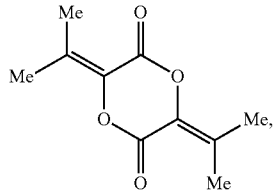

(MJX011)

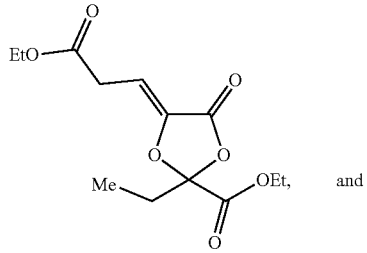

(MJX012)

and

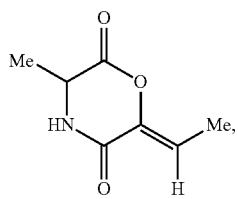

(MJX013)

or a pharmaceutically acceptable salt thereof.

In another aspect, the disclosure provides, a pharmaceutical composition of a compound described herein, or a pharmaceutically acceptable salt thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, the disclosure provides a method for treating or preventing an age-related disease or disorder associated with increased activity of ATP synthase, mTOR signaling, or a combination thereof, comprising administering to the mammal a compound described herein. In some embodiments, the disease or disorder is aging or an aging-related disease or disorder in a mammal.

In another aspect, the disclosure provides a method for slowing aging or extending lifespan in a mammal, comprising administering to the mammal a compound described herein, or a pharmaceutically acceptable salt thereof.

In one aspect, the disclosure provides a method for treating an aging-related disease in a mammal, comprising administering to the mammal a compound described herein, or a pharmaceutically acceptable salt thereof.

In some embodiments, $R^1$ and $R^2$ are taken together with the intervening atoms to form a fused 5-, 6-, or 7-membered ring containing 0-3 N atoms and 0-3 O atoms in the ring, wherein the fused 5-, 6-, or 7-membered ring is substituted with halo, —CN, —OH, oxo, unsubstituted or substituted alkyl, unsubstituted or substituted haloalkyl, unsubstituted or substituted alkene, unsubstituted or substituted alkyne, unsubstituted or substituted alkoxy, unsubstituted or substituted heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, or —$CO_2$(alkyl).

In some embodiments, the fused 5-, 6-, or 7-membered ring contains 0-2 N atoms and 0-2 O atoms in the ring. In some embodiments, the fused 5-, 6-, or 7-membered ring contains 1-2 N atoms and 1-2 O atoms in the ring. In some embodiments, the fused 5-, 6-, or 7-membered ring contains 0 N atoms and 0 O atoms, 1 N atoms and 0 O atoms, 2 N atoms and 0 O atoms, 3 N atoms and 0 O atoms, 0 N atoms and 1 O atoms, 0 N atoms and 2 O atoms, 0 N atoms and 3 O atoms, 1 N atoms and 1 O atoms, 2 N atoms and 1 O atoms, 1 N atoms and 2 O atoms, or 2 N atoms and 2 O atoms.

In some embodiments, the fused 5-, 6-, or 7-membered ring is substituted with halo, —OH, oxo, unsubstituted or substituted alkyl, unsubstituted or substituted haloalkyl, unsubstituted or substituted alkene, unsubstituted or substituted alkoxy, unsubstituted or substituted heteroalkyl, unsubstituted or substituted monocyclic carbocycle, unsubstituted or substituted monocyclic heterocycle, or —$CO_2$(alkyl).

In certain aspects, the present disclosure provides methods of slowing aging, extending lifespan, or treating an aging-related disease in a subject, comprising administering a compound as disclosed herein.

Methods of Use

Caloric restriction (CR) extends lifespan among all members of the animal kingdom (e.g., mammals). For example, in mice, a 50% increase in lifespan has been noted from CR. Studies suggest that the increase in longevity observed for CR may be a result of decreased ATP in an organism. Therefore, restricting ATP production in an organism may provide a route to increase longevity in mammals (S. Arbor, Nov. 5, 2018, Where and How in the mTOR Pathway Inhibitors Fight Aging: Rapamycin, Resveratrol, and Metformin, DOI: 10.5772/intechopen.79338).

The mTOR signaling pathway represents a master regulator of the effects of CR. For example, mTOR signaling contributes to the increase of, for example, protein synthesis, inflammation, lipogenesis, which contribute poorly to increasing longevity. However, mTOR signaling regulates the inhibition of, for example, autophagy, lysosomal biogenesis, and mitochondrial biogenesis, which also contribute poorly to increasing longevity. Therefore, inhibiting mTOR signaling represents plausible option for increasing longevity in an organism. Furthermore, many compounds that inhibit TOR signaling, such as, for example, rapamycin, metformin, and resveratrol, have been shown to increase longevity in mammals (S. Arbor, Nov. 5, 2018, Where and How in the mTOR Pathway Inhibitors Fight Aging: Rapamycin, Resveratrol, and Metformin, DOI: 10.5772/intechopen.79338).

In some embodiments, the present invention is directed to a compound disclosed herein for use in treating, inhibiting, or reducing aging of a subject; treating, inhibiting, or reducing an age-related symptom in a subject; treating, inhibiting, or reducing an age-related disease in a subject; increasing the lifespan of a subject; or treating, inhibiting, or reducing cardiac hypertrophy and/or myocardial infarction in a subject. In some embodiments, the compound is a ketobutyrate compound. In some embodiments, the ketobutyrate compound is alpha-ketobutyrate or alpha-ketobutyric acid. In some embodiments, the age-related symptom is cholesterol build-up, stiffening of arterial walls, increased blood pressure, immunosenescence, muscle loss, bone loss, arthritis, osteoporosis, memory loss, hearing loss, visual decline, increased wrinkles, hair loss, hair thinning, hair graying, decreased stress resistance, dementia, loss of hearing, loss of vision, loss of mobility, loss of muscle strength, loss of stamina, frailty, fatigue, increased susceptibility to infection, dry skin, wrinkled skin, altered sleep patterns, altered circadian cycles, metabolic changes, biochemical changes, or the like. In some embodiments, the age-related symptom is hair loss, hair thinning, hair graying, loss of mobility, loss of stamina, fatigue, increased susceptibility to infection, a metabolic change, or a biochemical change. In some embodiments, the age-related disease is a cancer (e.g., gliomas, leukemia, lymphoma, breast cancer, prostate cancer, lung cancer, etc.), a neurodegenerative disease (e.g., Parkinson's disease, Alzheimer's disease, Huntington's disease, dementia, etc.), sarcopenia, osteopenia, osteoporosis, arthritis, atherosclerosis, cardiovascular disease, hypertension, cataracts, presbyopia, glaucoma, type 2 diabetes, metabolic syndrome, alopecia, chronic inflammation, immunosenescence, or the like, or an age-related condition such as cardiac hypertrophy, cardiomyopathy, heart failure, or cardiovascular disease. In some embodiments, the age-related disease is cardiac hypertrophy, heart failure, myocardial infarction, ischemia reperfusion injury, or Alzheimer's Disease.

Age-Related Diseases or Disorders

The disclosure provides for the slowing, inhibiting, forestalling or reversing of age-related diseases, disorders, or conditions. In some embodiments, the age-related or other diseases, disorders, or conditions include one or more of cardiovascular diseases, diabetes, atherosclerosis, obesity, cancer, infection, and neurological disorders. The disclosure provides prodrug compositions to treat and/or prevent age-related or other diseases, disorders or conditions. The methods include reversing age-related diseases, disorders, and conditions and correcting these pathological states resulting in an increased health span (years of good quality of life) and lifespan. In some embodiments, aging and age-related diseases or disorders include symptoms and/or conditions associated with aging. For example, immunosenescence includes symptoms such as reduced white blood cell count and reduced T-cell function, and chronic inflammation can include changes in cytokine profile (e.g., increased pro-inflammatory cytokines).

In some embodiments, the age-related disease is a disease or disorder often associated with aging. In some embodiments, age-related diseases or disorders include cancers (e.g., gliomas, leukemia, lymphoma, breast cancer, prostate cancer, lung cancer, and the like), neurodegenerative diseases or neurological disorder (e.g., Parkinson's disease, Alzheimer's disease, Huntington's disease, dementia, and the like), sarcopenia, osteopenia, osteoporosis, arthritis, atherosclerosis, cardiovascular disease, hypertension, cataracts, presbyopia, glaucoma, type 2 diabetes, metabolic syndrome, alopecia, chronic inflammation, immunosenescence, age-related visual decline, age-related hair loss, thinning, and/or graying, and the like.

Cell Proliferation Disease

Disclosed herein in some embodiments are methods of preventing or treating cell proliferation diseases, for example, in certain types of cancer. In some embodiments, the ATP synthase inhibitors, mTOR signaling inhibitors, or a combination thereof disclosed herein are used in the prevention or treatment of, for example, a carcinoma, a sarcoma, a lymphoma, a leukemia, a myeloma, or any combination thereof. In some embodiments, the cancer is glioma, leukemia, lymphoma, breast cancer, prostate cancer, or lung cancer. In some embodiments, the cancer is a solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In some cases, cancer progression is characterized by stages, or the extent of cancer in the body. Staging is usually based on the size of the tumor, the presence of cancer in the lymph nodes, and the presence of the cancer in a site other than the primary cancer site. Stages of cancer may include stage I, stage II, stage III, and stage IV. In some embodiments, the carcinoma, sarcoma, lymphoma, leukemia, myeloma, or any combination thereof is from any stage. In other embodiments, the carcinoma, sarcoma, lymphoma, leukemia, myeloma, or any combination thereof is a stage I cancer, a stage II cancer, or a stage III cancer.

In some embodiments, a compound described herein is administered to a subject having a stage I, stage II, stage III, or stage IV cancer. In some instances, a compound described herein is administered to a subject having a stage I, stage II, or stage III carcinoma, sarcoma, lymphoma, leukemia, myeloma, or any combination thereof.

In some embodiments, a compound disclosed herein further reduces the tumor burden in a subject. In some examples, the compound reduces tumor burden in the subject by at least 5%, at least 10%, at least 15%, at least 20%, at least 30%, at least 40%, at least 50%, or more. In some instances, tumor burden is reduced by about 5% to about 50%, by about 5% to about 25%, by about 10% to about 20%, or by about 10% to about 30%. In some instances, the level of tumor burden is relative to the level of tumor burden in a subject not treated with the compound.

In some instances, a compound disclosed herein further reduces tumor size and/or volume in a subject. In some cases, the compound reduces tumor size and/or volume (such as a colon tumor) in the subject by at least 5%, at least 10%, at least 15%, at least 20%, at least 30%, at least 40%, at least 50%, or more. In some instances, tumor size is reduced by about 5% to about 50%, by about 5% to about 25%, by about 10% to about 20%, or by about 10% to about 30%. In some instances, the tumor size is relative to the tumor size in a subject not treated with the compound.

In additional embodiments, a compound disclosed herein reduces effects of cachexia due to a tumor in a subject. In some examples, the compound reduces the effect of cachexia in the subject by at least 5%, at least 10%, at least 15%, at least 20%, at least 30%, at least 40%, at least 50%, or more. In some instances, the effect of cachexia is reduced by about 5% to about 50%, by about 5% to about 25%, by about 10% to about 20%, or by about 10% to about 30%. In some instances, the effect of cachexia is relative to the effect of cachexia in a subject not treated with the compound.

In other embodiments, a compound disclosed herein increases survival rates of a subject with a tumor. In some cases, the compound increases the survival rate of a subject with a tumor in the subject by at least 5%, at least 10%, at least 15%, at least 20%, at least 30%, at least 40%, at least 50%, or more. In some instances, survival rate is increased by about 5% to about 50%, by about 5% to about 25%, by about 10% to about 20%, or by about 10% to about 30%. In some instances, the survival rate is relative to the survival rate in a subject not treated with the compound.

Neurological Disorders

In some embodiments, the age-related disease or disorder is a neurological disorder. In some embodiments, the neurological disorder is Parkinson's disease, Multisystem Lewy body disease (MLBD), parkinsonism, dementia with Lewy bodies (DLB), pure autonomic failure (PA), Parkinson's disease dementia (PDD), multiple system atrophy, progressive supranuclear palsy, corticobasal degeneration, frontotemporal dementia, Alzheimer's disease without Parkinson's disease, atypical parkinsonism, α-synuclein- or tau-related neuropathy, Lewy neurites or neuronal cell loss in substantia nigra, or α-synuclein-positive Lewy bodies. In some embodiments, the neurological disorder includes a movement disorders (e.g., movement disorders caused by a neurological disorder). In some embodiments, the neurological disorder is a movement disorder caused by the neurological disorder. In some embodiments, the neurological disorder is ataxia, Parkinson's disease, or multiple system atrophy (MSA). In some embodiments, the neurological disorder is Parkinson's disease or multiple system atrophy (MSA). In some embodiments, the neurological disorder is Parkinson's disease. In some embodiments, the neurological disorder is MSA.

Movement Disorders

In some embodiments, the age-related disease or disorder is a movement disorder with symptoms such as tremors, muscle rigidity, slow movement, and/or postural instability. In some instances, movement disorders are caused by a neurological disorder. In some instances, movement disorders include, but are not limited to, Parkinson's disease, MSA, progressive supranuclear palsy, viral parkinsonism, essential tremor, toxin-induced parkinsonism, arteriosclerotic parkinsonism, Parkinsonism-dementia complex of Guam, and normal pressure hydrocephalus (NPH). In some instances, treatment with certain drugs may induce movement disorder symptoms.

Cardiovascular Diseases

In some embodiments, the age-related disease or disorder is an age-related heart condition. In some embodiments, the age-related heart condition is cardiac hypertrophy, cardiomyopathy, heart failure, cardiac hypertrophy, cardiomyopathy, heart failure, or cardiovascular disease or disorder.

In some embodiments, the age-related disease or disorder is a cardiovascular disease or cardiovascular disorder. In some embodiments, the cardiovascular disease is a coronary artery diseases (CAD) (e.g., angina and myocardial infarction), stroke, heart failure, hypertensive heart disease, rheumatic heart disease, cardiomyopathy, abnormal heart rhythms, congenital heart disease, valvular heart disease, carditis, aortic aneurysms, peripheral artery disease, thromboembolic disease, or venous thrombosis. In some embodiments, the cardiovascular disease is CAD, stroke, or peripheral artery disease. In some embodiments, the cardiovascular disease is atherosclerosis (i.e., narrowing of an artery due to build-up of plaque).

In certain embodiments, provided herein is a compound for use in treating or preventing aging or an aging-related disease or disorder, wherein the compound has the structure of Formula (I), (Ia), (II), (III), (IV), (V), or (VI), or pharmaceutically acceptable salt thereof. In some embodiments, the aging or aging-related disease or disorder is associated with increased activity of ATP synthase, mTOR signaling, or a combination thereof. In some embodiments, the compounds represented by (I), (Ia), (II), (III), (IV), (V), and (VI), inhibit ATP synthase, mTOR signaling, or a combination thereof. In some embodiments, the compounds represented by (I), (Ia), (II), (III), (IV), (V), and (VI), extend a lifespan of a mammal. In some embodiments, the aging or aging-related disease or disorder is associated with decreased activity of AMPK (e.g., loss of AMPK signaling may be associated with reduced glucose sensitivity). In some embodiments, the compounds represented by (I), (Ia), (II), (III), (IV), (V), and (VI), activate or increase AMPK activity. In some embodiments, the compounds represented by (I), (Ia), (II), (III), (IV), (V), and (VI) inhibit ATP synthase, inhibit mTOR signaling, increase AMPK activity, or a combination thereof.

In another aspect, provided herein is a method for treating or preventing an age-related disease or disorder associated with increased activity of ATP synthase, mTOR signaling, or a combination thereof, comprising administering to the mammal a compound represented by Formula (I), (Ia), (II), (III), (IV), (V), or (VI). In some embodiments, the disease or disorder is aging or an aging-related disease or disorder in a mammal.

In another aspect, provided herein is a method for slowing aging or extending lifespan in a mammal, comprising administering to the mammal a compound represented by Formula (I), (Ia), (II), (III), (IV), (V), or (VI).

In another aspect, provided herein is a method for treating an aging-related disease in a mammal, comprising administering to the mammal a compound represented by Formula (I), (Ia), (II), (III), (IV), (V), or (VI).

In certain embodiments, provided herein is a compound for use in treating or preventing aging or an aging-related disease or disorder, wherein the compound has the structure of Formula (IA), (IAA), (IAA'), (IIA), (IIIA), (IVA), (VA), or (VIA), or pharmaceutically acceptable salt thereof. In some embodiments, the aging or aging-related disease or disorder is associated with increased activity of ATP synthase, mTOR signaling, or a combination thereof. In some embodiments, the compounds represented by (IA), (IAA), (IAA'), (IIA), (IIIA), (IVA), (VA), or (VIA), inhibit ATP synthase, mTOR signaling, or a combination thereof. In some embodiments, the compounds represented by (IA), (IAA), (IAA'), (IIA), (IIIA), (IVA), (VA), or (VIA), extend a lifespan of a mammal. In some embodiments, the aging or aging-related disease or disorder is associated with decreased activity of AMPK (e.g., loss of AMPK signaling may be associated with reduced glucose sensitivity). In some embodiments, the compounds represented by (IA), (IAA), (IAA'), (IIA), (IIIA), (IVA), (VA), or (VIA), activate or increase AMPK activity. In some embodiments, the compounds represented by (IA), (IAA), (IAA'), (IIA), (IIIA), (IVA), (VA), and (VIA), inhibit ATP synthase, inhibit mTOR signaling, increase AMPK activity, or a combination thereof.

In another aspect, provided herein is a method for treating or preventing an age-related disease or disorder associated with increased activity of ATP synthase, mTOR signaling, or a combination thereof, comprising administering to the mammal a compound represented by Formula (IA), (IAA), (IAA'), (IIA), (IIIA), (IVA), (VA), or (VIA). In some embodiments, the disease or disorder is aging or an aging-related disease or disorder in a mammal.

In another aspect, provided herein is a method for slowing aging or extending lifespan in a mammal, comprising administering to the mammal a compound represented by Formula (IA), (IAA), (IAA'), (IIA), (IIIA), (IVA), (VA), or (VIA).

In another aspect, provided herein is a method for treating an aging-related disease in a mammal, comprising administering to the mammal a compound represented by Formula (IA), (IAA), (IAA'), (IIA), (IIIA), (IVA), (VA), or (VIA).

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "acetal" is art-recognized and may be represented by the general formula

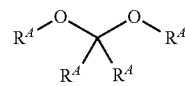

wherein each $R^A$ independently represents hydrogen or a hydrocarbyl, such as alkyl, or any occurrence of $R^A$ taken together with another and the intervening atom(s) complete a carbocycle or heterocycle having from 4 to 8 atoms in the ring structure.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkyC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. Co alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

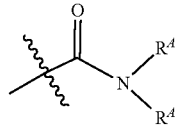

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

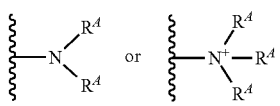

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "boron" as used herein with respect to a substituent on an organic compound, is art-recognized and refers to a group —B($R^A$)$_2$, wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

The term "boronic ester" or "boronate ester" as used herein is art-recognized and refers to a group —B(O$R^A$)$_2$, wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

The term "carbamate" is art-recognized and refers to a group

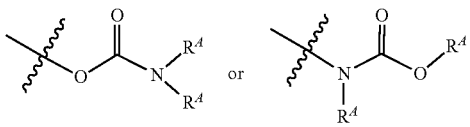

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—$R^A$, wherein $R^A$ represents a hydrocarbyl group.

The term "carboxy", as used herein, refers to a group represented by the formula —CO$_2$H.

The term "diazo", as used herein, refers to a group represented by the formula =N=N.

The term "disulfide" is art-recognized and refers to a group —S—S—$R^A$, wherein $R^A$ represents a hydrocarbyl group.

The term "enol ester", as used herein, refers to a group —C(O)O—C($R^A$)=C($R^A$)$_2$ wherein $R^A$ represents a hydrocarbyl group.

The term "ester", as used herein, refers to a group —C(O)O$R^A$ wherein $R^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like. In some embodiments, illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Other examples of monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 1-4 N atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like. In some embodiments, a heterocyclyl contains 2 O atoms in the ring. In some embodiments, a heterocyclyl contains 1 N atom and 1 O atom.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "orthoester" as used herein is art-recognized and refers to a group —C(OR$^A$)$_3$, wherein each R$^A$ independently represents hydrogen or a hydrocarbyl, such as alkyl, or any occurrence of R$^A$ taken together with another and the intervening atom(s) complete a heterocycle having from 4 to 8 atoms in the ring structure.

The term "phosphoester", as used herein, refers to a group —P(O$_2$)OH.

The term "phosphodiester", as used herein, refers to a group —P(O$_2$)OR$^A$ wherein R$^A$ represents a hydrocarbyl group.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "selenide", as used herein, is equivalent to an ether, wherein the oxygen is replaced with a selenium.

The term "selenoxide" is art-recognized and refers to the group —Se(O)—R$^A$, wherein R$^A$ represents a hydrocarbyl.

The term "siloxane" is art-recognized and refers to a group with an Si—O—Si linkage, such as the group —Si(R$^A$)$_2$—O—Si—(R$^A$)$_3$, wherein each R$^A$ independently represents hydrogen or hydrocarbyl, such as alkyl, or both R$^A$ taken together with the intervening atom(s) complete a heterocycle having from 4 to 8 atoms in the ring structure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

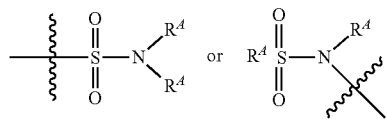

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^A$, wherein $R^A$ represents a hydrocarbyl.

The term "thioalkyl", as used herein, refers to an alkyl group substituted with a thiol group.

The term "thioester", as used herein, refers to a group —$C(O)SR^A$ or —$SC(O)R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

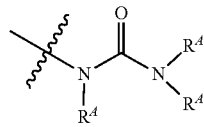

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula L The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Synthesis of Exemplary Compounds of the Disclosure

Synthetic Procedure and Characterization Data for MJX001

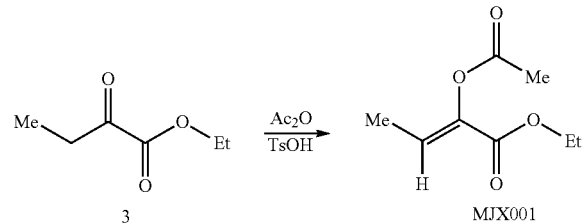 [SMILES: "Ac2O" ; CCOC(=O)C(=O)CC ; "TsOH" ; C/C=C(\OC(C)=O)C(=O)OCC]

A solution of ethyl 2-oxobutanoate 3 (1.0 g, 7.7 mmol) and p-toluenesulfonic acid monohydrate (30 mg, 0.16 mmol) in acetic anhydride (2.0 mL) was stirred in a sealed tube at 140° C. for 24 h. The mixture was diluted with ethyl acetate, washed with saturated sodium bicarbonate, water and then brine, dried over anhydrous sodium sulfate and filtered. The filtrate was concentrated in vacuo. The resulting residue was purified by flash chromatography on silica gel to give MJX001 (0.7 g, 53%). $^1$H NMR (400 MHz, CDCl$_3$) δ 6.62 (q, J=7.1 Hz, 1H), 4.22 (q, J=7.2 Hz, 2H), 2.25 (s, 3H), 1.74 (d, J=7.2 Hz, 3H), 1.29 (t, J=7.2 Hz, 3H); $^{13}$C NMR (100 MHz, CDCl$_3$) δ 168.7, 161.7, 139.2, 126.8, 61.3, 20.2, 14.1, 11.4; HRMS (ESI, m/z): calcd for C$_8$H$_{13}$O$_4$ ([M+H]$^+$): 173.0814, Found: 173.0807.

Synthetic Procedure and Characterization Data for MJX002

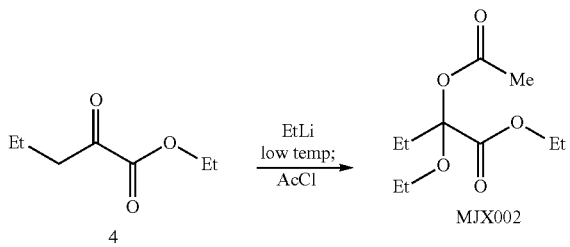 [SMILES: "AcCl" ; CCCC(=O)C(=O)OCC ; "EtLilow temp;" ; CCOC(=O)C(CC)(OCC)OC(C)=O]

A solution of diethyl oxalate 4 (10.5 g, 72 mmol) in dry ether (70 ml) was cooled to −78° C. and ethyllithium (50 mmol, 1.0 M, freshly prepared from EtBr and lithium) was added dropwise. The mixture was slowly warmed to −65° C. and then recooled to −78° C., and acetyl chloride (5.93 g, 76 mmol) in ether (5 ml) was added. The mixture was warmed to 21° C. and after 30 min, triethylamine (0.35 ml) was added. Water was then added and the organic phase was separated. The aqueous phase was then extracted with ether. The combined ether solution was washed with brine, dried over anhydrous sodium sulfate and filtered. The filtrate was concentrated in vacuo. The resulting residue was purified by flash chromatography on silica gel (hexanes/ethyl acetate) to give MJX002 (1.57 g, 10%). $^1$H NMR (400 MHz, CDCl$_3$) δ 4.26-4.21 (m, 2H), 3.71-3.59 (m, 2H), 2.18-2.12 (m, 1H), 2.08 (s, 3H), 2.02-1.97 (m, 1H), 1.28 (t, J=7.2 Hz, 3H), 1.21 (t, J=7.0 Hz, 3H), 0.89 (t, J=7.6 Hz, 3H); C NMR (100 MHz, CDCl$_3$) δ 169.1, 167.6, 101.8, 61.6, 59.7, 28.0, 21.0, 15.2, 14.0, 6.8; HRMS (ESI, m/z): calcd for C$_{10}$H$_{17}$O$_5$ ([M−H]$^−$): 217.1082, Found: 217.1077.

Synthetic Procedure and Characterization Data for MJX003

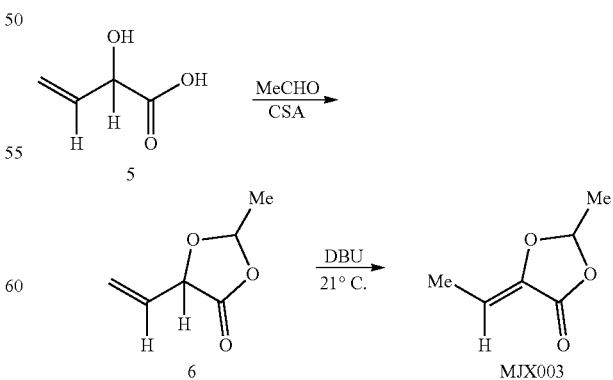

Camphorsulfonic acid (0.23 g, 1.0 mmol) was added to a solution of 2-hydroxy-3-butenoic acid 5 (2.05 g, 20.0 mmol) and acetaldehyde (5.1 ml, 66%, 60 mmol) in benzene (15 mL). The mixture was stirred overnight and then diluted with diethyl ether, washed with saturated sodium bicarbonate and brine, dried over anhydrous sodium sulfate, and gently concentrated under reduced pressure. The resulting residue was purified by flash choreography on silica gel (pentane/diethyl ether) to give compound 6 (2.05 g, 80%). Compound 6 (2.05 g, 16 mmol) was then dissolved in dry diethyl ether (20 ml) and cooled to 0° C. To this solution was added dropwise 1,8-diazabicyclo[5.4.0]undec-7-ene (DBU, 2.44 g, 16 mmol) with stirring. The mixture was allowed to be warmed to 21° C. and stirred for 25 min. Water was then added and the organic phase was separated. The aqueous was extracted with diethyl ether. The combined ether solution was washed with brine, dried over anhydrous sodium sulfate and filtered. The filtrate was concentrated in vacuo. The resulting residue was purified by flash chromatography on silica gel (pentane/Et$_2$O) to give MJX003 (0.41 g, 20%). $^1$H NMR (400 MHz, CDCl$_3$) δ 5.90 (q, J=5.1 Hz, 1H), 5.65 (q, J=7.3 Hz, 1H), 1.76 (d, J=7.2 Hz, 3H), 1.58 (d, J=5.2 Hz, 1H); $^{13}$C NMR (100 MHz, CDCl$_3$) δ 162.8, 138.7, 105.8, 102.4, 21.5, 10.7; HRMS (ESI, m/z): calcd for C$_6$H$_7$O$_3$ ([M−H]$^−$): 127.0401, Found: 127.0401.

Synthetic procedure and Characterization data for MJX004

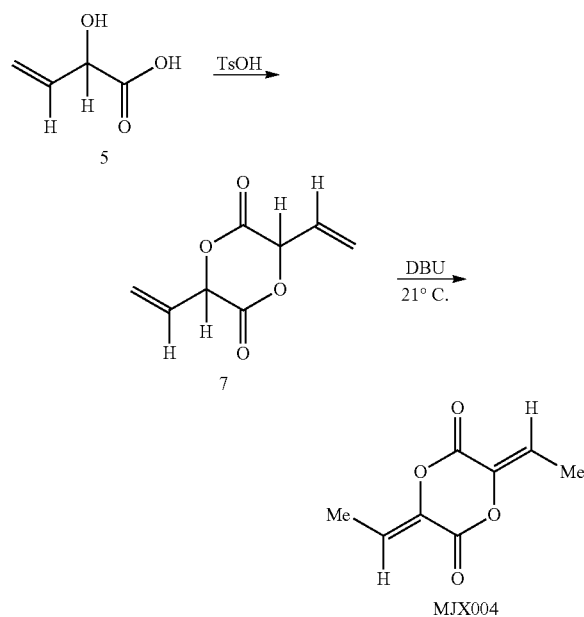

A mixture of 2-hydroxy-3-butenoic acid 5 (4.1 g, 40 mmol) and p-toluenesulfonic acid monohydrate (0.77 g, 4.0 mmol) in toluene (400 ml) was heated at reflux for 24 h and the water which formed was removed continuously by using a Dean-Stark apparatus. The mixture was cooled to 21° C., washed successively with saturated sodium bicarbonate, water and then brine, dried over anhydrous sodium sulfate and filtered. The filtrate was concentrated in vacuo. The resulting residue was purified by flash chromatography on silica gel (hexanes/ethyl acetate) to give compound 7 (1.23 g, 37%). Compound 7 (1.23 g, 7.3 mmol) was then dissolved in dry diethyl ether (20 ml) and cooled to 0° C. To this solution was added dropwise diisopropyl ethyl amine (DIEA, 1.3 ml, 7.5 mmol) with stirring. The mixture was allowed to warm to 21° C. and stirred for 1 h. The precipitated product was collected by filtration, carefully washed with cooled ether and dried in vacuo to give product MJX004 (0.57 g, 46%) as a white solid. H NMR (400 MHz, CDCl$_3$) δ 6.53 (q, J=7.3 Hz, 1H), 1.93 (d, J=7.2 Hz, 3H); $^{13}$C NMR (100 MHz, CDCl$_3$) δ 153.9, 136.8, 125.3, 11.1; FIRMS (ESI, m/z): calcd for C$_8$H$_7$O$_4$ ([M−H]$^−$): 167.0350, Found: 167.0350.

Synthetic Procedure and Characterization Data for MJX005

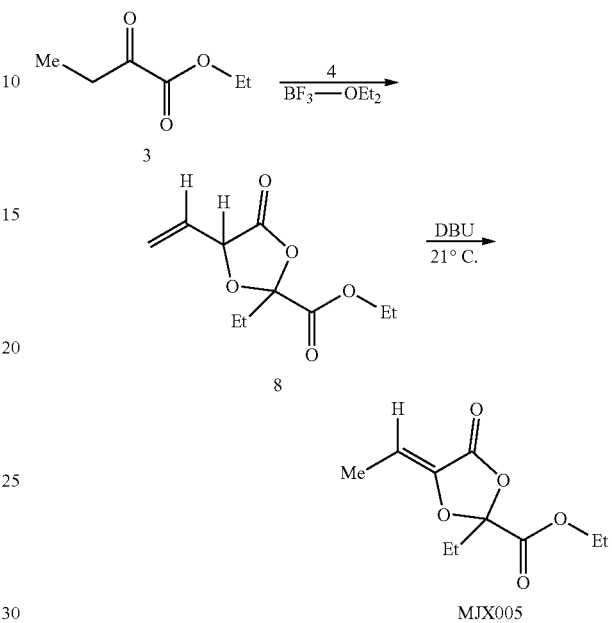

A mixture of ethyl 2-oxobutanoate 3 (4.0 g, 31 mmol), 2-hydroxy-3-butenoic acid 4 (6.3 g, 62 mmol) and 48% BF$_3$.Et$_2$O (36 ml) was stirred for 2 h at 21° C. Then the mixture was carefully added to saturated aqueous sodium bicarbonate and extracted with dichloromethane. The combined dichloromethane solution was washed with water and brine, dried over anhydrous sodium sulfate, and concentrated under reduced pressure. The resulting residue was purified by flash chromatography on silica gel (hexanes/ ethyl acetate) to give compound 8 (2.63 g, 40%). The compound 8 (2.63 g, 12.3 mmol) was then dissolved in dry diethyl ether (20 ml) and cooled to 0° C. To this solution was added dropwise DBU (1.87 g, 12.3 mmol) with stirring. The mixture was allowed to be warmed to 21° C. and stirred for 30 min. Water was then added and the organic phase was separated. The aqueous was extracted with diethyl ether. The combined ether solution was washed with brine, dried over anhydrous sodium sulfate and filtered. The filtrate was concentrated in vacuo. The resulting residue was purified by flash chromatography on silica gel (hexanes/ethyl acetate) to give MJX005 (1.47 g, 56%). $^1$H NMR (400 MHz, CDCl$_3$) δ 5.71 (q, J=7.3 Hz, 1H), 4.27 (q, J=7.2 Hz, 2H), 2.21-2.14 (m, 2H), 1.80 (d, J=7.6 Hz, 3H), 1.30 (t, J=7.0 Hz, 3H), 1.00 (t, J=7.4 Hz, 3H); $^{13}$C NMR (100 MHz, CDCl$_3$) δ 165.8, 162.0, 138.4, 107.1, 106.0, 62.7, 27.8, 13.9, 10.8, 5.7; HRMS (ESI, m/z): calcd for C$_{10}$H$_{13}$O$_5$ ([M−H]$^−$): 213.0769, Found: 213.0768.

Synthetic procedure and Characterization data for MJX006

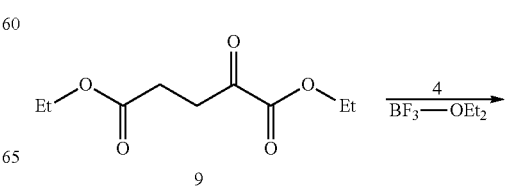

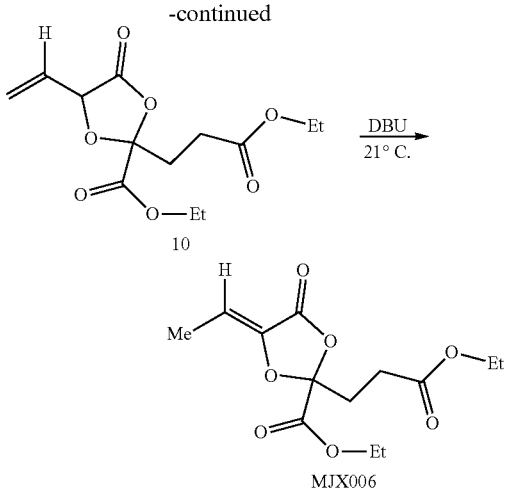

A mixture of 2-hydroxy-3-butenoic acid 4 (0.45 g, 4.4 mmol), diethyl 2-oxopentanedioate 9 (diethyl α-ketoglutarate, 0.45 g, 2.2 mmol) and 48% BF$_3$.Et$_2$O (5 ml) was stirred for 12 h at 21° C. Then the mixture was carefully added to saturated sodium bicarbonate aqueous, extracted with dichloromethane. The combined dichloromethane solution was washed with water and brine, dried over anhydrous sodium sulfate, and concentrated under reduced pressure. The resulting residue was purified by flash choreography on silica gel (hexanes/Et$_2$O) to give compound 10 (0.22 g, 35%). The compound 10 (0.22 g, 0.77 mmol) was then dissolved in dry ether (10 ml) and cooled to 0° C. To this solution was added dropwise DBU (0.12 g, 0.79 mmol) with stirring. The mixture was allowed to be warmed to 21° C. and stirred for 30 min. Water was then added and the organic phase was separated. The aqueous was extracted with ether. The combined ether solution was washed with brine, dried over anhydrous sodium sulfate and filtered. The filtrate was concentrated in vacuo. The resulting residue was purified by flash chromatography on silica gel (hexanes/Et$_2$O) to give MJX006 (68 mg, 31%). $^1$H NMR (400 MHz, CDCl$_3$) δ 5.75 (q, J=7.5 Hz, 1H), 4.26 (q, J=7.2 Hz, 2H), 4.14 (q, J=7.2 Hz, 2H), 2.56-2.52 (m, 2H), 2.47-2.43 (m, 2H), 1.79 (d, J=7.6 Hz, 3H), 1.30 (t, J=7.2 Hz, 3H), 1.25 (t, J=7.2 Hz, 3H); $^{13}$C NMR (100 MHz, CDCl$_3$) δ 171.8, 165.3, 161.4, 138.0, 107.9, 104.6, 63.0, 60.9, 29.6, 26.9, 14.1, 13.9, 10.9; HRMS (ESI, m/z): calcd for C$_{13}$H$_{17}$O$_7$ ([M−H]$^−$): 285.0980, Found: 285.0972.

Synthetic Procedure and Characterization Data for MJX007

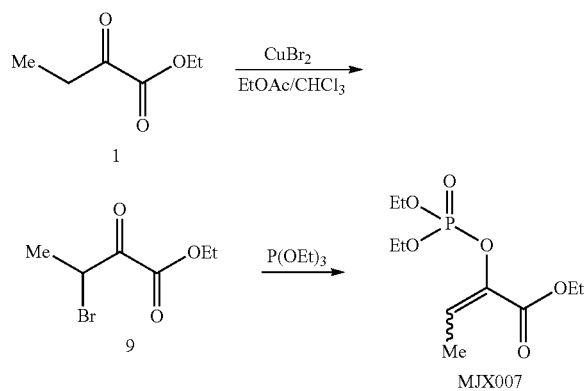

To a suspension of CuBr$_2$ (6.7 g, 30 mmol) in ethyl acetate (40 mL) was added ethyl 2-oxobutanoate 1 (1.3 g, 10.0 mmol) in chloroform (20 mL) and the mixture was refluxed for 12 h. The mixture was cooled to 21° C., filtered through a silica plug and the filtrate evaporated on rotary evaporator carefully with the temperature of the water bath no more than 30° C. yielding 9 (1.82 g, 87%) which was sufficiently pure for the following step. To compound 9 was added dropwise triethyl phosphite (1.52 g, 9.1 mmol) at 0° C. under argon. The mixture was stirred at 21° C. for 1 h, then 50° C. for 30 min. The resulting mixture was purified by flash chromatography on silica gel (hexanes/ethyl acetate) to give MJX007 (2.08 g, 90%). H NMR (400 MHz, CDCl$_3$) δ 6.52 (qd, J=7.2, 2.0 Hz, 1H), 4.28-4.20 (m, 6H), 1.86 (dd, J=7.2, 2.8 Hz, 3H), 1.35 (td, J=7.0, 1.2 Hz, 6H), 1.29 (t, J=7.2 Hz, 3H); $^{13}$C NMR (100 MHz, CDCl$_3$) δ 162.2 (d, J=1.5 Hz), 138.7 (d, J=8.4 Hz), 125.7 (d, J=6.1 Hz), 64.5 (d, J=6.1 Hz), 61.4, 16.0 (d, J=7.3 Hz), 14.1, 11.6 (d, J=1.9 Hz); $^{31}$P NMR (162 MHz, CDCl$_3$) δ −5.73; HRMS (ESI, m/z): calcd for C$_{10}$H$_{20}$O$_6$P ([M+H]$^+$): 267.0992, Found: 267.0980.

Synthetic Procedure and Characterization Data for MJX008

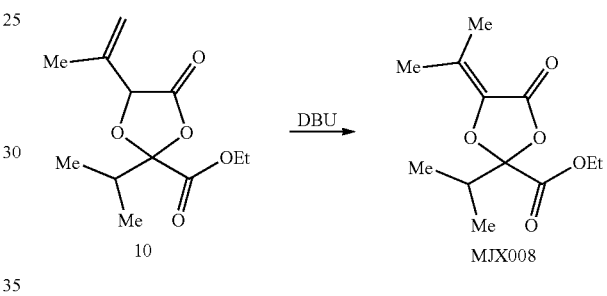

The dioxolanone 10 (1.12 g, 4.6 mmol), which was prepared from the corresponding hydroxyl ester and the α-keto ester by a method similar to that used to prepare compound 6, was dissolved in dry ether (20 ml) and cooled to 0° C. To this solution was added dropwise DBU (70 mg, 0.46 mmol) with stirring. The mixture was warmed to 21° C. and stirred for 30 min. The solvent was concentrated in vacuo and the resulting residue was purified by flash chromatography on silica gel (hexanes/Et$_2$O) to give MJX008 (0.76 g, 68%). H NMR (400 MHz, CDCl$_3$) δ 4.27 (q, J=7.1 Hz, 2H), 2.55-2.48 (m, 1H), 2.09 (d, J=0.8 Hz, 3H), 1.86 (d, J=0.8 Hz, 3H), 1.30 (t, J=7.0 Hz, 3H), 1.00 (d, J=7.2 Hz, 3H), 0.98 (d, J=6.8 Hz, 3H); $^{13}$C NMR (100 MHz, CDCl$_3$) δ 166.4, 161.6, 132.5, 123.8, 106.3, 62.4, 32.7, 19.3, 16.7, 15.2, 14.4, 14.0; HRMS (ESI, m/z): calcd for C$_{12}$H$_{19}$O$_5$ ([M+H]+): 243.1227, Found: 243.1207.

Synthetic Procedure and Characterization Data for MJX009

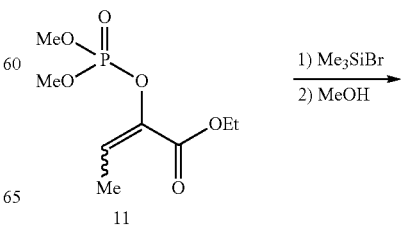

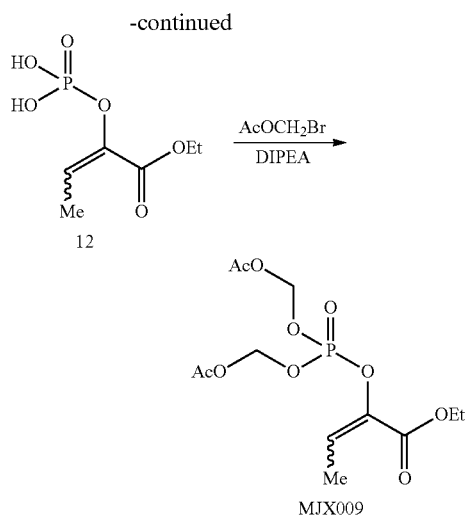

A solution of 11 (1.0 g, 4.2 mmol), prepared by a method similar to that used to prepare MJX007, in DCM (20 mL) was cooled to 0° C. and bromotrimethylsilane (3.2 ml, 24.3 mmol) was added dropwise under argon. The mixture was warmed to 21° C. and stirred for 12 h. The solvent was evaporated under vacuum and the resulting residue was then dissolved in methanol (20 mL). The mixture was stirred at 21° C. for 2 h. Evaporation of all volatiles under vacuum gave phosphoric acid 12 which was sufficiently pure for the following step. Compound 12 was dissolved in acetonitrile (20 mL) and cooled to 0° C. Diisopropylethylamine (DIPEA, 8.0 ml) was then added followed by the dropwise addition of acetoxymethyl bromide (6.2 g, 40.5 mmol). The mixture was stirred in the dark for 24 h at 21° C., all volatiles were removed under vacuum and the resulting residue was purified by flash chromatography on silica gel (hexanes/ethyl acetate) to give MJX009 (1.07 g, 72%). $^1$H NMR (400 MHz, CDCl$_3$) δ 6.56 (qd, J=7.3, 1.6 Hz, 1H), 5.76-5.71 (m, 4H), 4.25 (q, J=7.1 Hz, 2H), 2.14 (s, 6H), 1.87 (dd, J=7.2, 2.8 Hz, 3H), 1.31 (t, J=7.2 Hz, 3H); $^{13}$C NMR (100 MHz, CDCl$_3$) δ 169.2, 161.8 (d, J=1.6 Hz), 138.4 (d, J=8.8 Hz), 126.4 (d, J=6.5 Hz), 82.9 (d, J=5.0 Hz), 61.8, 20.7, 14.1, 11.7 (d, J=1.5 Hz); $^{31}$P NMR (162 MHz, CDCl$_3$) δ −9.16; HRMS (ESI, m/z): calcd for C$_{12}$H$_{20}$O$_{10}$P ([M+H]$^+$): 355.0789, Found: 355.0760.

Synthetic Procedure and Characterization Data for MJX010

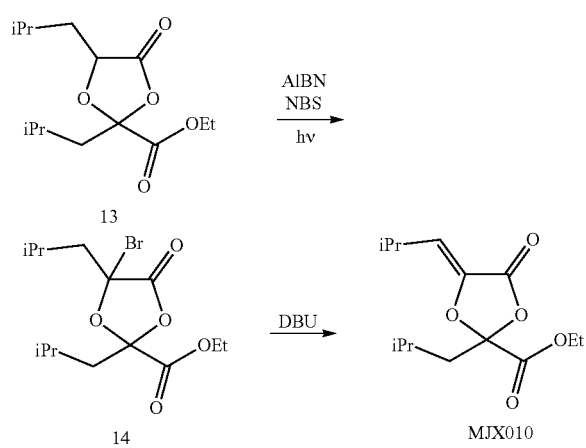

To a solution of 13 (2.4 g, 8.8 mmol), which was prepared from the corresponding hydroxyl ester and the α-keto ester by a method similar to that used to prepare compound 6, in carbon tetrachloride (20 ml), were added NBS (1.62 g, 9.1 mmol) and AIBN (43 mg, 0.26 mmol) under argon. The pale-yellow suspension was refluxed for 30 min under irradiation with white light (normal-pressure 200 W lamp) to give a colorless suspension. The insoluble succinimide was removed by filtration and the solid was washed with carbon tetrachloride. The solution concentrated under vacuum to give the dioxolanone 14 which was sufficiently pure for the following step. Compound 14 was dissolved in THF (30 mL) and cooled to 0° C. DBU (1.48 g, 9.7 mmol) was then added dropwise. The mixture was warmed to 21° C. and stirred for 2 h. The solvent was removed under vacuum and the resulting residue was dissolved in ethyl acetate, washed with hydrochloride (1 N), saturated sodium bicarbonate and brine, dried over anhydrous sodium sulfate and filtered. The filtrate was concentrated in vacuo and the resulting residue was purified by flash chromatography on silica gel (hexanes/ethyl acetate) to give MJX010 (0.98 g, 41%). $^1$H NMR (400 MHz, CDCl$_3$) δ 5.59 (d, J=8.8 Hz, 1H), 4.29-4.23 (m, 2H), 2.75-2.69 (m, 1H), 2.13-2.01 (m, 2H), 1.90-1.83 (m, 1H), 1.30 (t, J=7.2 Hz, 3H), 1.08 (d, J=6.5 Hz, 3H), 1.06 (d, J=6.5 Hz, 3H), 0.98 (d, J=6.4 Hz, 6H); $^{13}$C NMR (100 MHz, CDCl$_3$) δ 166.0, 162.4, 135.8, 119.1, 105.9, 62.7, 42.3, 25.8, 23.6, 23.5, 22.9, 21.94, 21.93, 14.0; HRMS (ESI, m/z): calcd for C$_{14}$H$_{23}$O$_5$ ([M+H]$^+$): 271.1540, Found: 271.1537.

Synthetic Procedure and Characterization Data for MJX011

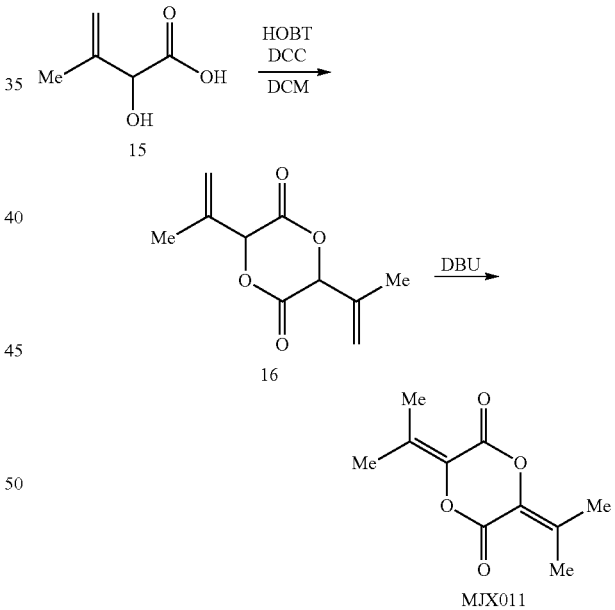

To a suspension of hydroxybenzotriazole (HOBT, 5.71 g, 36 mmol) and dicyclohexyl carbodimide (DCC, 7.43 g, 36 mmol) in DCM (200 mL) was dropwise added a solution of compound 15 (2.84 g, 24.5 mmol) in DCM (20 mL) under argon, and the mixture was stirred at 21° C. for 12 h. The reaction mixture was filtered, and the solvent was removed under reduced pressure. The resulting residue was purified by flash chromatography on silica gel (hexanes/ethyl acetate) to give the dilactone 16 (1.20 g, 50%). Compound 16 (1.20 g, 6.12 mmol) was then dissolved in dry ether (30 ml) and cooled to 0° C. To this solution was added dropwise DBU (100 mg, 0.66 mmol) with stirring. The mixture was warmed to 21° C. and stirred for 30 min. The solvent was evaporated under vacuum and the resulting residue was purified by flash chromatography on silica gel (hexanes/ethyl acetate) to give MJX011 (1.05 g, 88%). $^1$H NMR (400 MHz, CDCl$_3$) δ 2.21 (s, 6H), 2.00 (s, 6H); $^3$C NMR (100 MHz, CDCl$_3$) δ 156.4, 139.6, 131.4, 20.1, 19.9; HRMS (ESI, m/z): calcd for C$_{10}$H$_{13}$O$_4$ ([M+H]$^+$): 197.0808, Found: 197.0801.

Synthetic Procedure and Characterization Data for MJX012

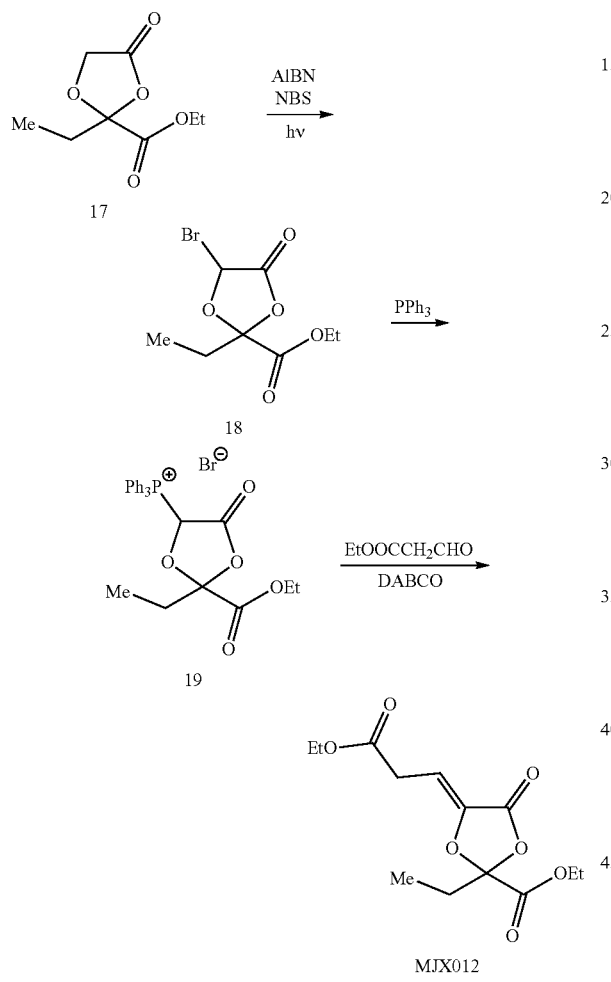

To a solution of 17 (1.88 g, 10 mmol) which was prepared from the corresponding hydroxyl ester and the α-keto ester by a method similar to that used to prepare compound 6, in carbon tetrachloride (20 ml), were added NBS (1.89 g, 10.6 mmol) and AIBN (50 mg, 0.30 mmol) under argon. The pale-yellow suspension was refluxed for 30 min under irradiation with white LED strip lights (100 cm, 12 W, purchased from https://www.superbrightleds.com, product code NFLS-CW60X3-WHT-LC2) to give a colorless suspension. The insoluble succinimide was removed by filtration and the solid washed with carbon tetrachloride. The solution was concentrated under vacuum to give the bromo dioxolanone 18 which was sufficiently pure for the following step. Compound 18 was dissolved in dry toluene (25 ml) and a solution of triphenylphosphine (2.62 g, 10 mmol) in toluene (5 mL) was then added. The resulting mixture was stirred at 50° C. for 12 h. The toluene was removed under vacuum to give the phosphonium salt 19. Compound 19 was suspended in benzene (30 ml) and heated to reflux under argon. Then DABCO (1.18 g, 10.5 mmol) in benzene (5 ml) was added dropwise and the mixture was stirred for 10 min before the addition of ethyl 3-oxopropanate (2.32 g, 20 mmol) in benzene (5 ml). The mixture was then refluxed for 10 h. The mixture was cooled to 21° C. and the solid was removed by filtration. The filtrate was evaporated in vacuum and the resulting residue was purified by flash chromatography on silica gel (hexanes/ethyl acetate) to give MJX012 (0.43 g, 15%). $^1$H NMR (400 MHz, CDCl$_3$) 5.87 (t, J=7.4 Hz, 1H), 4.27 (qd, J=7.2, 0.8 Hz, 2H), 4.17 (q, J=7.1 Hz, 2H), 3.26 (dd, J=7.6, 1.2 Hz, 2H), 2.22-2.14 (m, 2H), 1.30 (t, J=6.6 Hz, 3H), 1.27 (t, J=6.4 Hz, 3H), 1.00 (t, J=7.2 Hz, 3H); $^3$C NMR (100 MHz, CDCl$_3$) δ 169.6, 165.4, 161.3, 139.0, 106.4, 103.1, 62.9, 61.2, 31.2, 27.7, 14.1, 13.9, 5.7; HRMS (ESI, m/z): calcd for C$_{13}$H$_{17}$O$_7$ ([M−H]$^−$): 285.0980, Found: 285.0972.

Synthetic Procedure and Characterization Data for MJX013

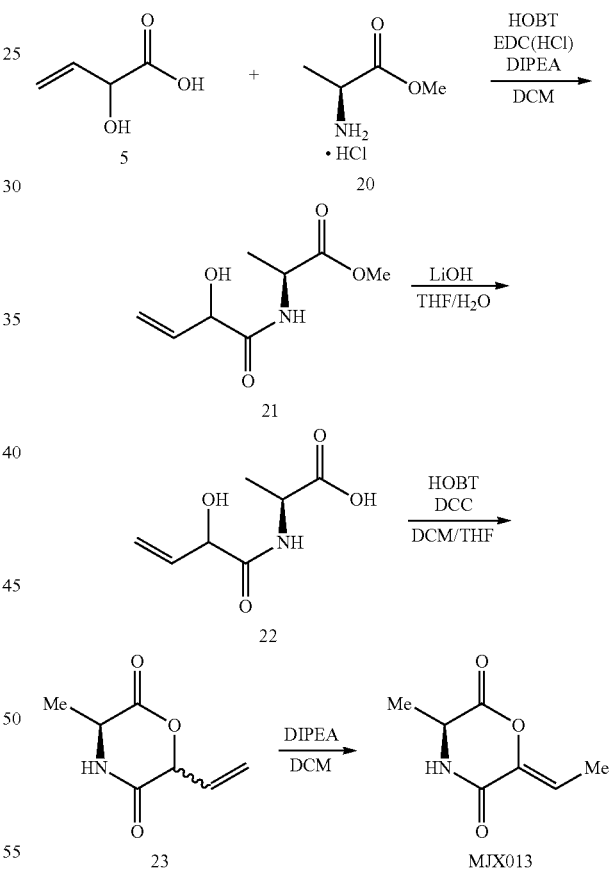

A suspension of L-alanine methyl ester hydrochloride 20 (1.40 g, 10.0 mmol), 5 (1.02 g, 10.0 mmol) and hydroxybenzotriazole (HOBT, 2.38 g, 15.0 mmol) in dichloromethane (DCM, 30 ml) was cooled to 0° C. and diisopropylethylamine (DIPEA, 9.0 ml) was added dropwise under argon. After the reaction had stirred for 5 minutes, a suspension of 1-ethyl-3-(3-dimethylamino-propyl)carbodiimide hydrochloride EDC (HCl) (2.88 g, 15.0 mmol) in DCM (5 ml) was added. The mixture was warmed to 21° C. and stirred for 24 h. The reaction mixture was then diluted with DCM (200 ml), washed with saturated sodium bicarbonate solution (3×50 ml), dried over anhydrous sodium sulfate, and concentrated under reduced pressure. The resulting residue was purified by flash chromatography on silica gel (hexanes/ethyl acetate) to give compound 21 (0.94 g, 50%).

To a solution of compound 21 (0.94 g, 5.0 mmol) dissolved in THF (20 ml) was added an aqueous LiOH solution (1.0 M, 5.5 ml). The reaction mixture was stirred for 3 h at 21° C., diluted with aqueous HCl (1.0 N, 60 ml) and extracted with ethyl acetate (5×50 ml). The combined ethyl acetate solution was washed with brine, dried over anhydrous sodium sulfate, and concentrated under reduced pressure to give compound 22 (0.87 g, 100%) which was sufficiently pure for the following step.

To a suspension of HOBT (1.19 g, 7.5 mmol) and dicyclohexyl carbodiimide (DCC, 1.55 g, 7.5 mmol) in DCM (30 mL) was dropwise added a solution of compound 22 (0.87 g, 5.0 mmol) in THF (8 mL) under argon, and the mixture was stirred at 21° C. for 12 h. The reaction mixture was filtered, and the solvent was removed under reduced pressure. The resulting residue was purified by flash chromatography on silica gel (hexanes/ethyl acetate) to give compound 23 (0.30 g, 77%).

Compound 23 (0.30 g, 1.93 mmol) was dissolved in dry DCM (15 ml) and cooled to 0° C. To this solution was added dropwise DIPEA (0.35 ml, 2.0 mmol) with stirring. The mixture was warmed to 21° C. and stirred for 12 h. The solvent was evaporated under vacuum and the resulting residue was purified by flash chromatography on silica gel (hexanes/ethyl acetate) to give MJX013 (0.22 g, 73%). $^1$H NMR (500 MHz, CDCl$_3$) δ 7.71 (br s, 1H), 7.26 (q, J=7.3 Hz, 1H), 4.33 (qd, J=7.0, 1.0 Hz, 1H), 1.85 (d, J=7.0 Hz, 3H), 1.58 (d, J=7.0 Hz, 3H); $^{13}$C NMR (125 MHz, CDCl$_3$) δ 164.5, 159.8, 141.1, 118.7, 49.6, 19.5, 10.4; HRMS (ESI, m/z): calcd for C$_7$HNO$_3$ ([M−H]$^-$): 154.0510, Found: 154.0507.

Example 2: Anti-Aging Effect in *C. elegans*

The anti-aging effects of MJX001-MJX005 were tested in the nematode *Caenorhabditis elegans*. Worms of the N2 wildtype strain of *C. elegans* were age-synchronized by performing either a timed egg lay or an egg preparation (mix <100 gravid worms in 70 μl M9 buffer, 25 μl bleach and 5 μl 10 N NaOH). Once the worms reached day 1 of adulthood, they were picked onto NGM treatment plates containing 1.5% dimethyl sulfoxide (DMSO; Sigma D8418), 49.5 μM 5-fluoro-2'-deoxyuridine (FUDR, Sigma F0503), and either Y-ketobutyrate (Sigma K401) or one of the MJX series test compounds. All plates were adjusted to pH 6.0 (i.e., the same pH as the control plates) if necessary by the addition of NaOH. Once dry, the plates were seeded with OP50 *E. coli* as the *C. elegans* food source.

Figure 1B:
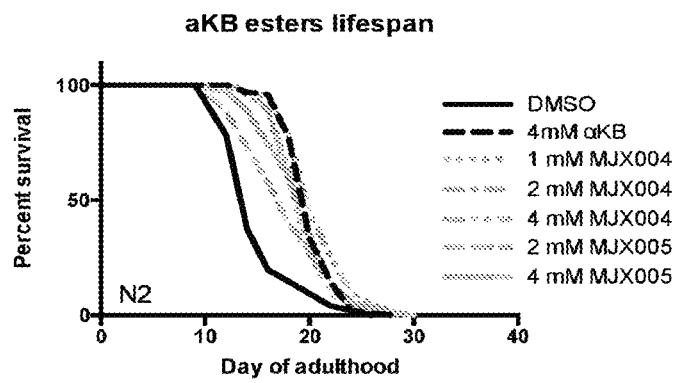
Figure 1C:
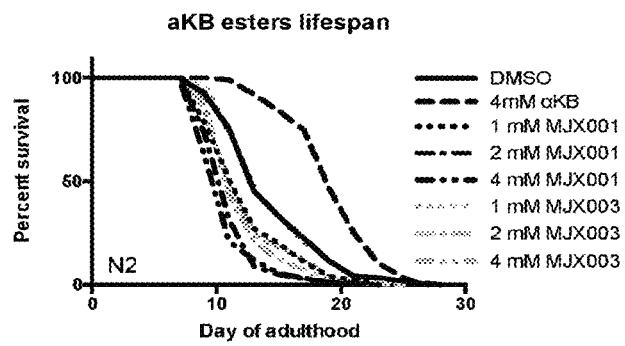

To assess survival of the worms, the animals were prodded with a platinum wire every 2-3 days, and those that failed to respond were scored as dead. Worms were moved to new plates every 4 days. All worms were maintained in a single humidified, temperature-controlled incubator at 20° C. Lifespan curves were generated and statistical analyses performed. As shown in FIGS. 1A-1C, MJX002, MJX004, and MJX005 each exhibited dose-dependent increases in lifespan, whereas MJX001 and MJX003 decreased *C. elegans* lifespan.

TABLE 1

Data from FIG. 1A

| Treatment: | DMSO | 4 mM aKB | 100 μM MJX002 | 300 μM MJX002 | 1 mM MJX002 | 4 mM MJX002 |
|---|---|---|---|---|---|---|
| mean lifespan | 11.7 | 17.7 | 11.9 | 13.2 | 12.2 | 16.4 |
| % increase |  | 51.0 | 1.9 | 13.0 | 4.2 | 40.0 |
| p-value (Log-Rank) |  | <0.0001 | 0.6511 | 0.001 | 0.1767 | <0.0001 |

TABLE 2

Data from FIG. 1B

| Treatment: | DMSO | 4 mM aKB | 1 mM MJX004 | 2 mM MJX004 | 4 mM MJX004 | 2 mM MJX005 | 4 mM MJX005 |
|---|---|---|---|---|---|---|---|
| mean lifespan | 15.3 | 20.4 | 19.7 | 20.0 | 21.1 | 18.2 | 19.6 |
| % increase |  | 33.3 | 28.7 | 30.9 | 38.0 | 19.1 | 27.7 |
| p-value (Log-Rank) |  | <0.0001 | <0.0001 | <0.0001 | <0.0001 | <0.0001 | <0.0001 |

TABLE 3

Data from FIG. 1C

| Treatment: | DMSO | 4 mM aKB | 1 mM MJX001 | 2 mM MJX001 | 4 mM MJX001 | 1 mM MJX003 | 2 mM MJX003 | 4 mM MJX003 |
|---|---|---|---|---|---|---|---|---|
| mean lifespan | 14.8 | 19.7 | 12.9 | 11.5 | 11.1 | 14.8 | 12.5 | 12.9 |
| % increase |  | 33.3 | −12.9 | −22.4 | −24.8 | −0.2 | −15.3 | −12.7 |
| p-value (Log-Rank) |  | <0.0001 | <0.0001 | <0.0001 | <0.0001 | 0.798 | <0.0001 | 0.0003 |

Example 3: Anti-Aging Effect in Rat Cardiomyocytes

The effects of MJX001-MJX005 on aging-related signaling pathways in mammalian cells were tested. Previous studies with α-ketobutyric acid have suggested that it may extend lifespan partly through inhibition of pyruvate dehydrogenase activity, leading to decreased mitochondrial oxidative phosphorylation and increased activity of the energy-sensing AMPK. The resulting increase in AMPK activity seems necessary for the lifespan extension effect of α-ketobutyric acid in C. elegans.

H9C2 rat cardiomyocyte cells were grown in DMEM media (ATCC #30-2002) supplemented with 10% FBS. Stock solutions of MJX series compounds were prepared in DMSO, while the stock solution of α-ketobutyrate was prepared in $dH_2O$. Cells were seeded in the afternoon at 70-80% confluency and the next morning treated with the indicated concentrations of compounds for the indicated times. Cells were then washed with ice-cold PBS and immediately lysed on ice with RIPA buffer. Lysates were clarified at 18,000 g at 4° C., the supernatants transferred to new tubes, mixed with 4 volume of 5×SDS-PAGE loading buffer, and heated for 10 minutes at 70° C. Lysates were then separated by SDS-PAGE using 4-12% Bis-Tris gels (Life Technologies) and transferred to PVDF membranes (Millipore) for western blotting analysis. All antibodies were purchased from Cell Signaling.

Figure 2A:
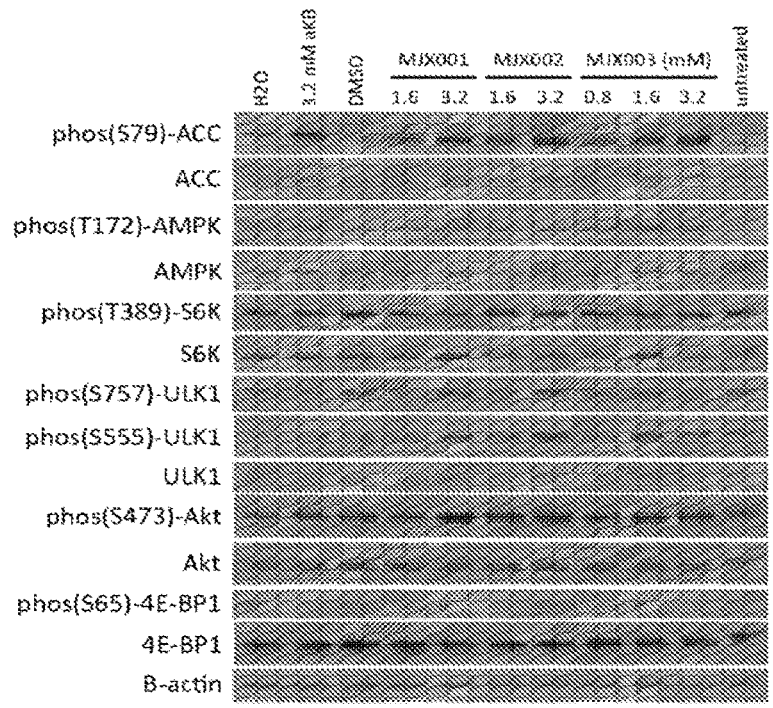
FIGS. 2A-2F show the effects of exemplary compounds of the present invention on signaling pathways in H9C2 rat cardiomyocytes.

As shown in FIG. 2A, MJX001, MJX002, and MJX003 each activate the AMPK signaling pathway in H9C2 rat cardiomyocytes. This is evidenced by the increased phosphorylation of the AMPK targets ACC (S79) and ULK1 (S555). Increased phosphorylation of T172 in AMPK itself was also observed with MJX003, which is also a marker of AMPK activation. On the other hand, MJX001, MJX002, and MJX003 had no significant effect on the mTORC1 targets S6K (T389), 4E-BP1 (S65), and ULK1 (S757) in H9C2 cells.

Figure 2B:
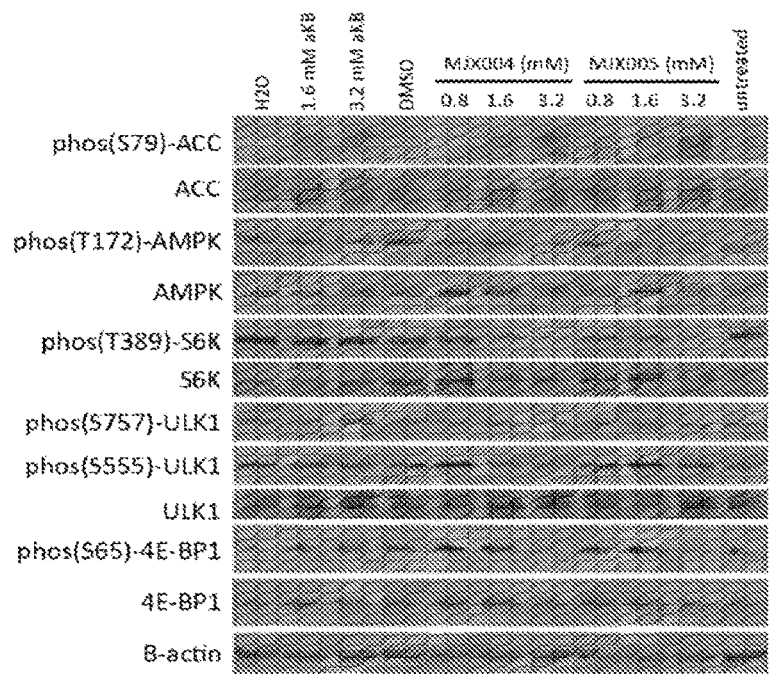

In contrast to MJX001-003, MJX004 and MJX005 not only activate the AMPK pathway but also inhibited mTORC1 signaling in H9C2 cells (FIG. 2B). This is evidenced by the increased phosphorylation of the AMPK targets ACC (S79) and ULK1 (S555), whereas the mTORC1 targets S6K (T389), 4E-BP1 (S65), and ULK1 (S757) all exhibited decreased phosphorylation.

Figure 2C:
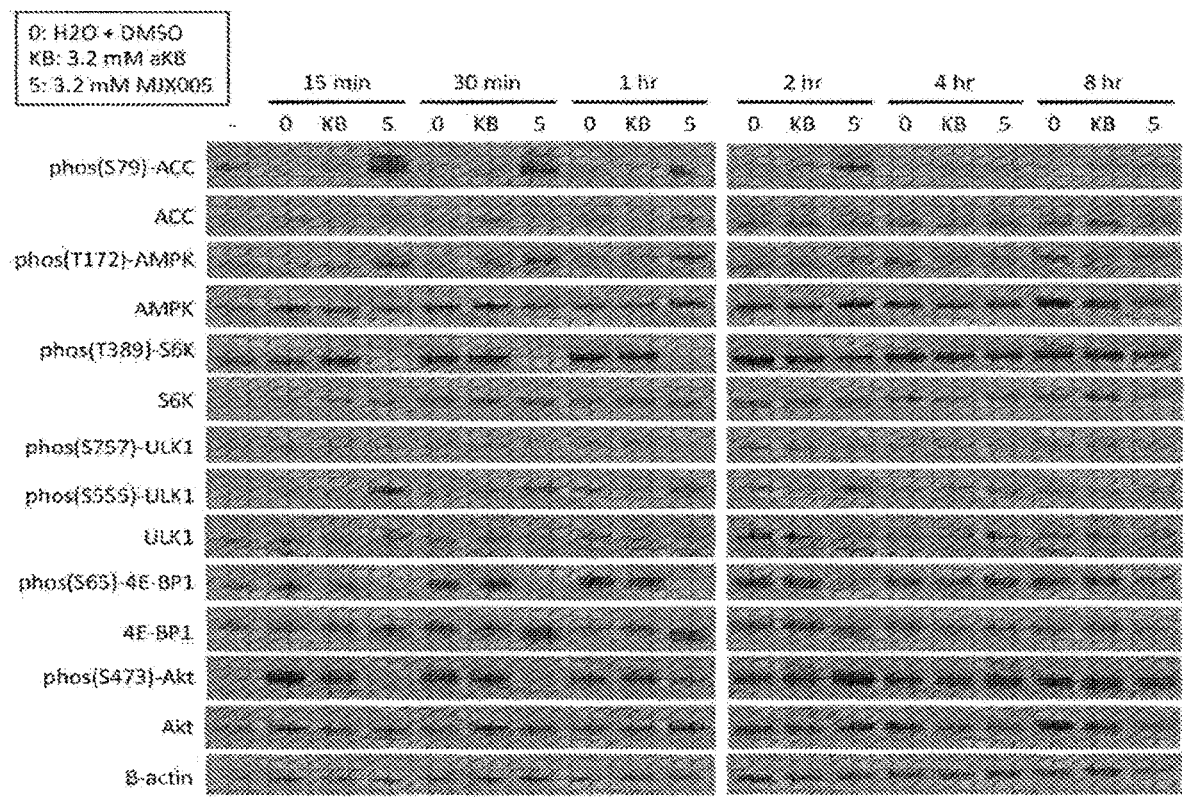
Figure 2D:
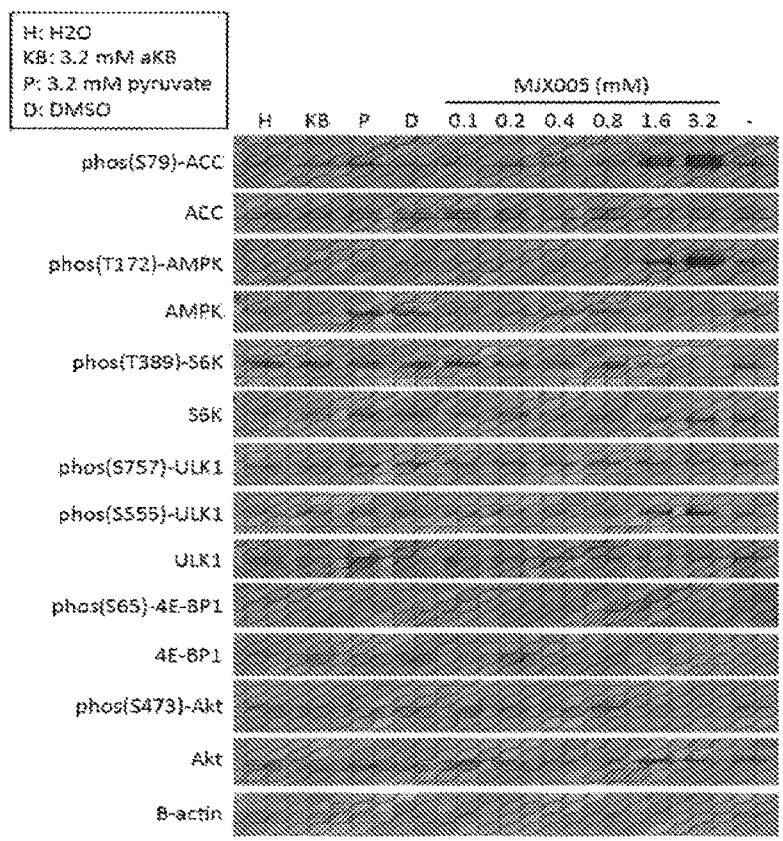

Not only does MJX005 exhibit more potent activation of AMPK than α-ketobutyrate as well as the added activity of mTOR inhibition, MJX005 also acts very rapidly. As shown in FIG. 2C, strong activation of AMPK and inhibition of mTOR signaling in H9C2 cells can be seen after only 15 minutes treatment with MJX005. Moreover, MJX005 inhibits both mTORC1 and mTORC2 activity, as demonstrated by the dramatic decrease in phosphorylation of S6K (T389), 4E-BP1 (S65), ULK1 (S757), and Akt (S473). Dose-response analysis indicates that millimolar concentrations of MJX005 are required for activation of AMPK and inhibition of mTOR signaling, as 0.8 mM or lower had no significant effect, 1.6 mM had a modest effect, and 3.2 mM had a strong effect (FIG. 2D).

Figure 2E:
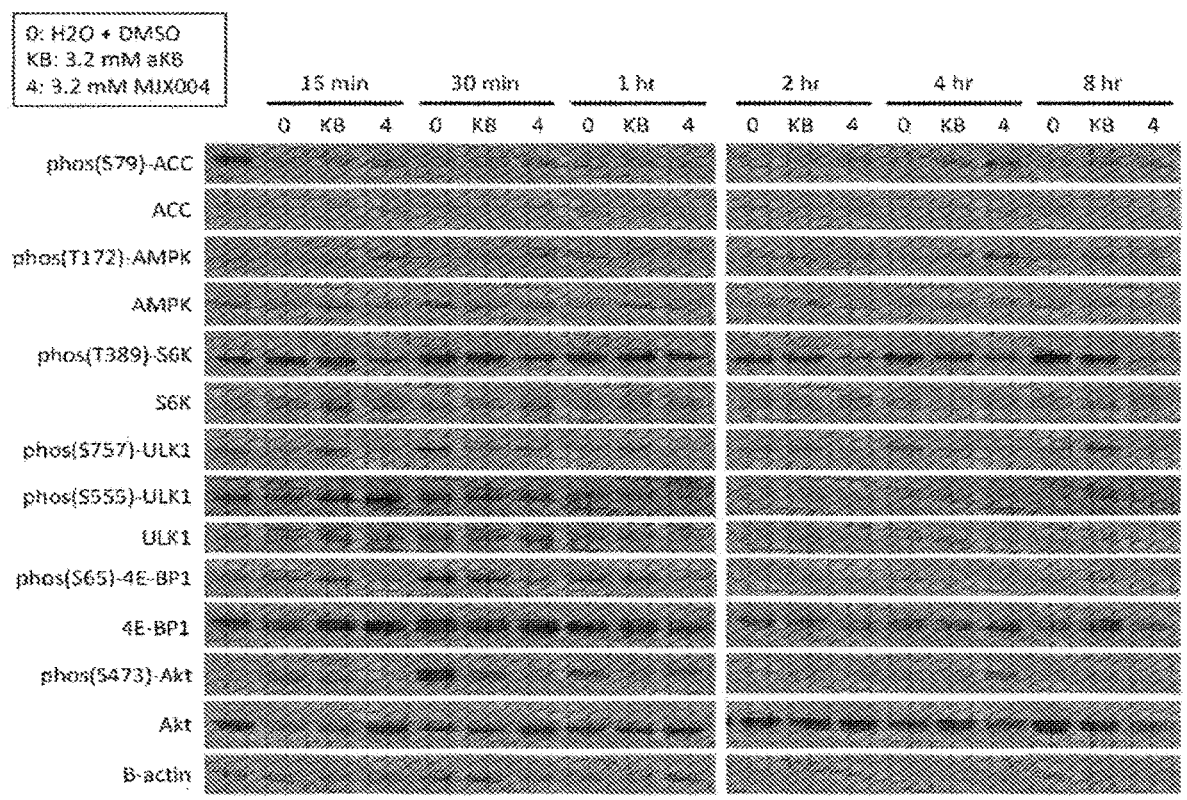

In contrast to MJX005, MJX004 exhibits a less potent but more prolonged activation of AMPK and inhibition of mTOR signaling (FIG. 2E). Whereas the effects of MJX005 on AMPK and mTOR were greatly diminished by 2 hr and largely absent at 4 hr and 8 hr (FIG. 2C), MJX004 showed strong activation of AMPK at 4 hr and sustained inhibition of mTORC1 at 4 and 8 hr (FIG. 2E). On the other hand, inhibition of mTORC2 as demonstrated by decreased phosphorylation of Akt (S473) by both MJX004 and MJX005 was strongest after just 15 and 30 minutes treatment, but recovered to normal levels by 2 hr and beyond.

Figure 2F:
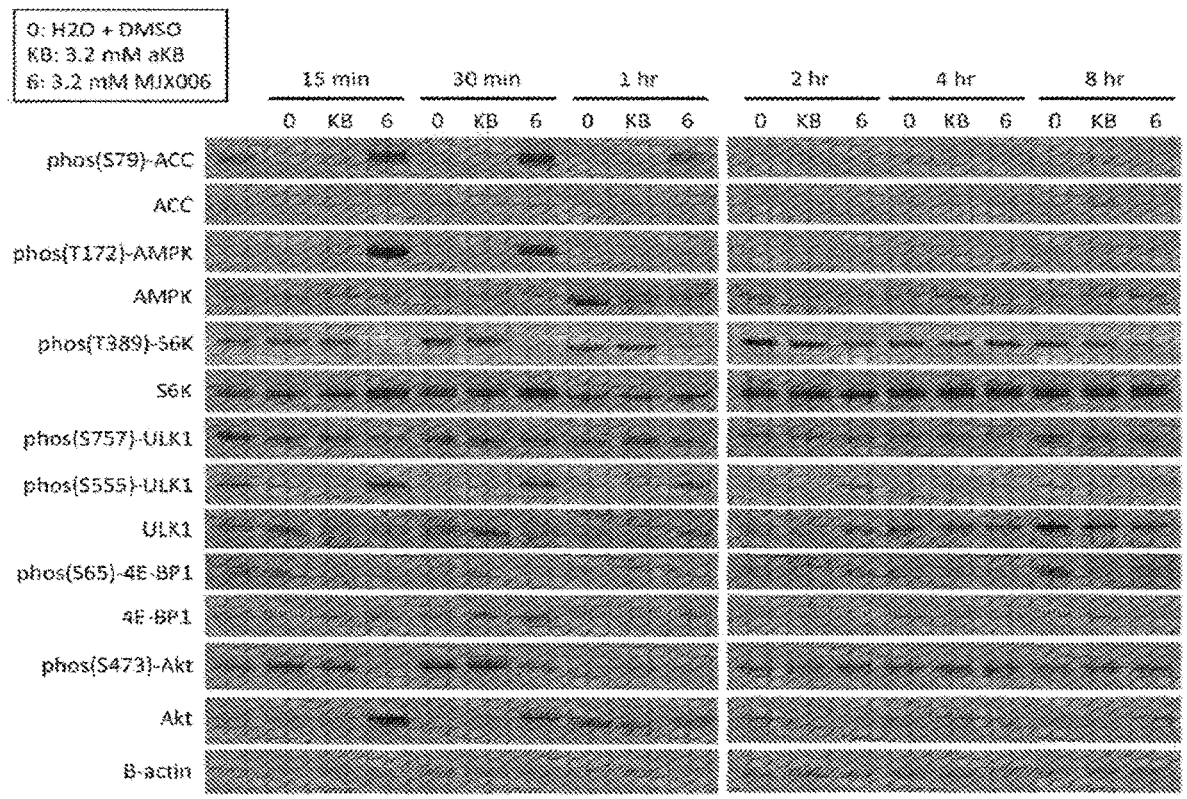

Interestingly, MJX006 appears to be similar in its ability to rapidly promote AMPK activity and inhibit mTORC1 and mTORC2 signaling in H9C2 cells (FIG. 2F). AMPK activation as demonstrated by increased phosphorylation of the AMPK targets ACC (S79) and ULK1 (S555) as well as of AMPK itself (T172) is highest at 15 and 30 minutes, is weaker but still evident at 1 hour, and has largely returned to baseline by 2 hours. Inhibition of mTOR as demonstrated by decreased phosphorylation of mTORC1 targets S6K (T389), 4E-BP1 (S65), and ULK1 (S757) and the mTORC2 target Akt (S473) exhibited similar kinetics. These results are in line with the expectation that MJX005 and MJX006 should hydrolyze much more rapidly than MJX004, suggesting that MJX005 and MJX006 might be useful as a fast acting treatment for acute conditions where activation of AMPK and inhibition of mTOR would be beneficial, whereas MJX004 is appears to be a slower release compound.

Example 4: Anti-Aging Effect in Mouse Liver Mitochondria

Figure 3:
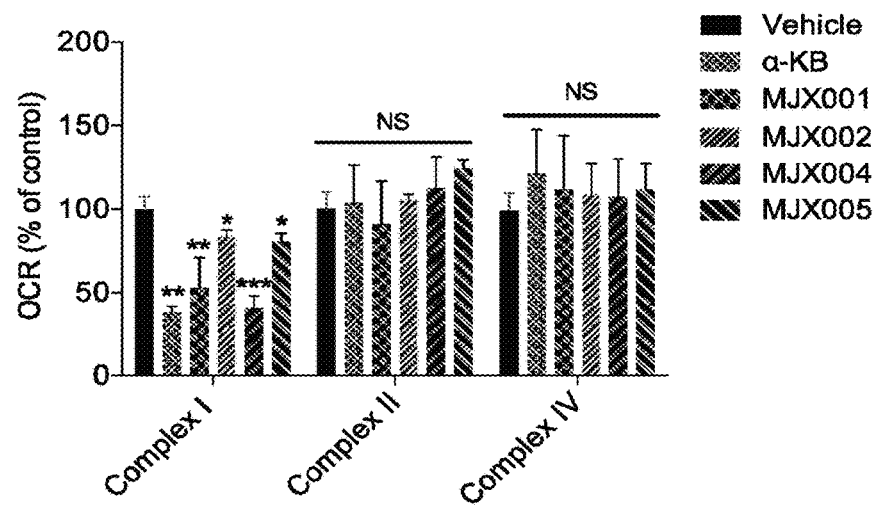
FIG. 3 show the effects of exemplary compounds of the present invention on oxygen consumption in mouse liver mitochondria.

These compounds were next evaluated in a seahorse platform to test whether they inhibit pyruvate-dependent respiration as α-KB does. Mitochondria were isolated from mouse liver. The oxygen consumption rate (OCR) was measured using a Seahorse XF-24 Analyzer (Seahorse Bioscience). For the electron flow assay, 10 mM sodium pyruvate, and 2 mM malate were provided for complex I respiration. 10 mM succinate, and 10 mM/100 M ascorbate/tetra-methylphenylenediamine were provided as substrates for complex II and complex IV respectively. All compounds were incubated with mitochondria for 10 minutes before measurement. All of the compounds inhibited respiration when pyruvate was provided as a respiratory substrate, but had no inhibitory effects when substrates for complex II or complex IV were provided (FIG. 3).

Example 5: Effects on Metabolic Pathways in Rat Cardiomyocytes

Figure 4:
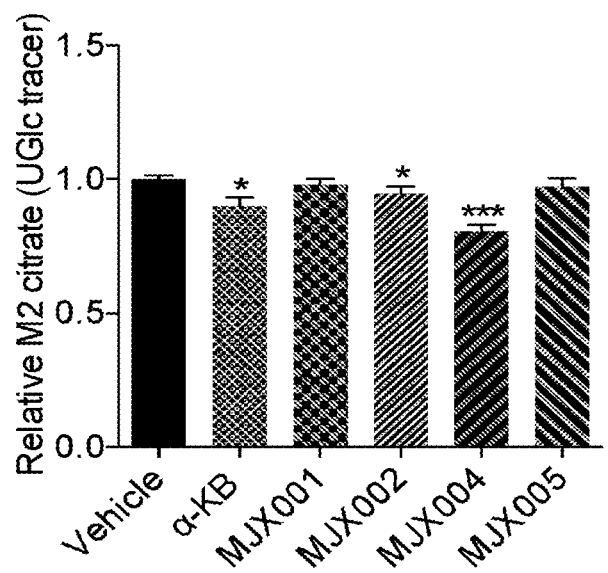
FIG. 4 show the effects of exemplary compounds of the present invention on citrate usage in H9C2 rat cardiomyocytes.

To evaluate the metabolic pathways in use, H9C2 Cells were cultured with designated compounds and medium containing [U-$^{13}C_6$]glucose for 24 h. Metabolites were extracted for LC-MS detection. Several compounds (MJX002 and MJX004) decreased M2 citrate as measured using [U-13C6]glucose as a tracer, indicating that glucose-derived pyruvate oxidation is inhibited by these compounds (FIG. 4).

Example 6: Toxicity Study

Figure 5A:
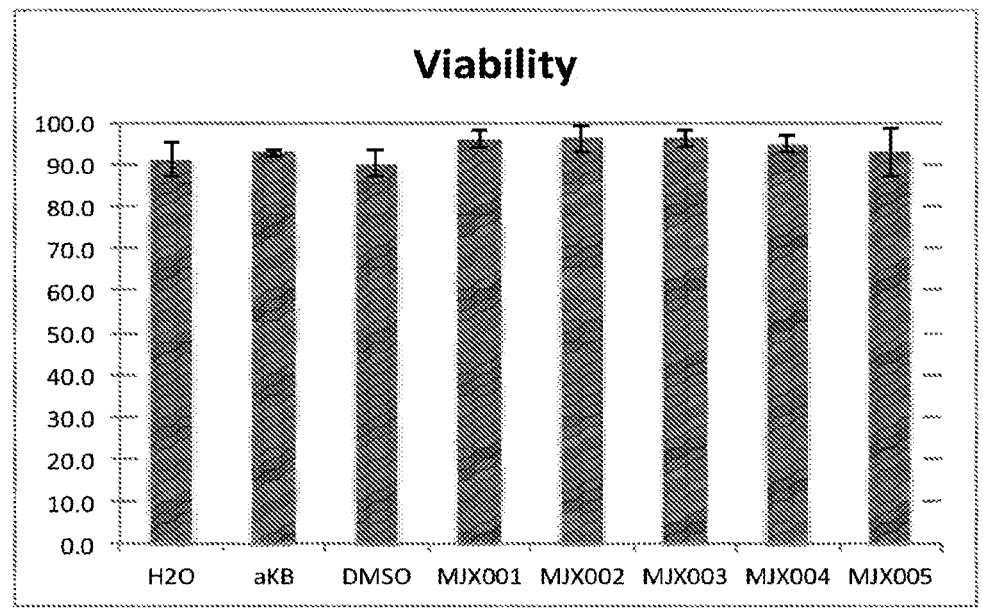
FIGS. 5A and 5B shows the effects of exemplary compounds of the present invention on the viability of H9C2 rat cardiomyocytes.
Figure 5B:
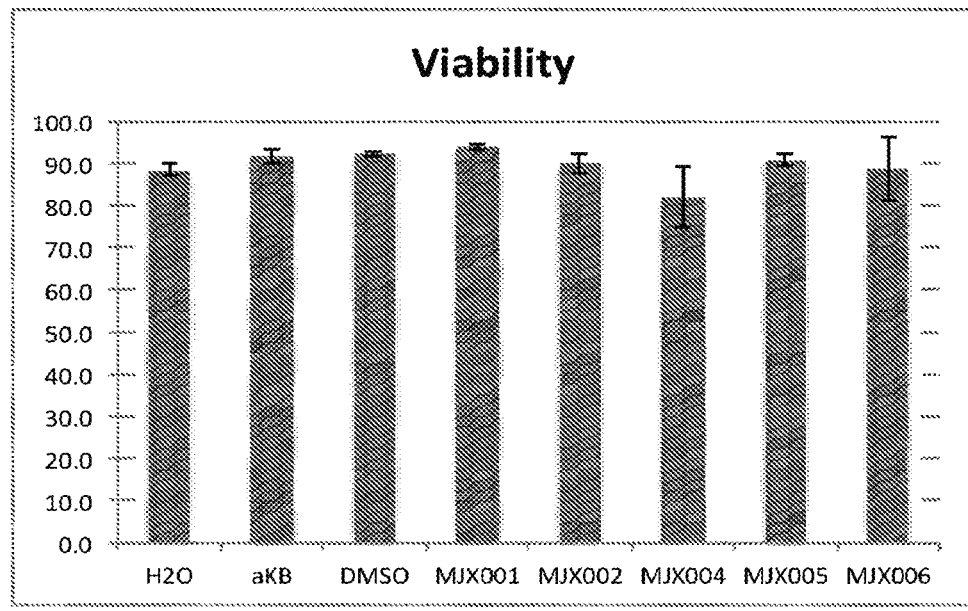
Figure 6A:
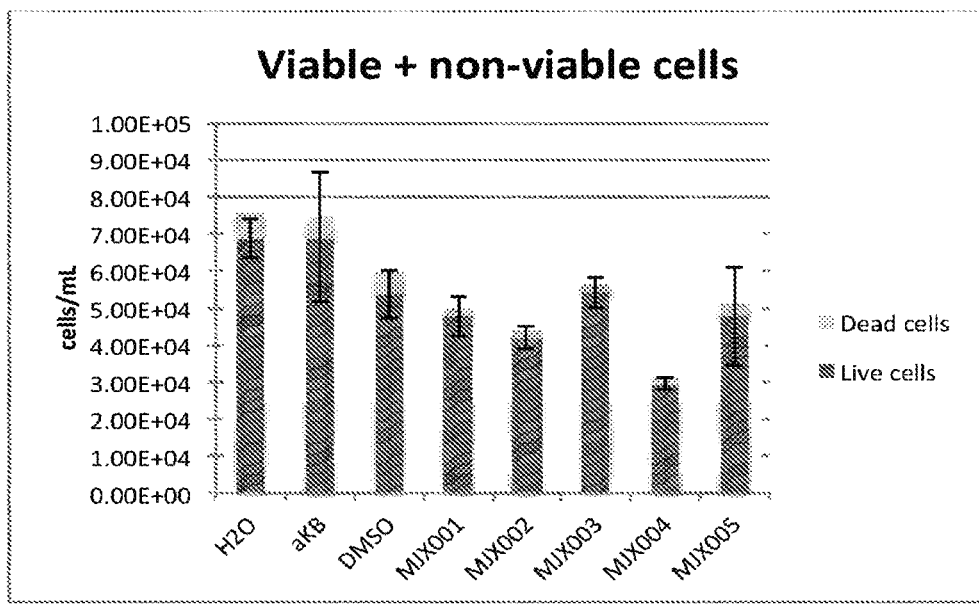
FIGS. 6A and 6B shows the effects of exemplary compounds of the present invention on the proliferation of H9C2 rat cardiomyocytes.
Figure 6B:
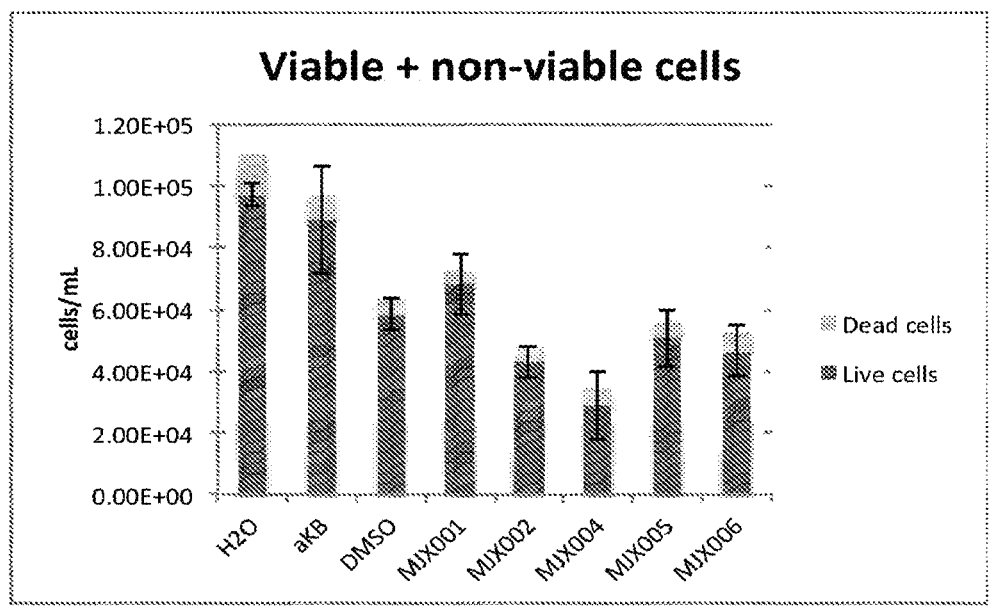

None of the compounds were toxic to H9C2 cells at 3.2 mM, the highest dose used in the assays (FIGS. 5A & 5B), although some compounds noticeably inhibited proliferation (FIGS. 6A & 6B). MJX004 had the strongest effect on proliferation, followed by MJX002, MJX005, and MJX006. This effect is not unexpected given that the compounds inhibit mTOR signaling, a major regulator of cell growth. The fact that MJX004 inhibits proliferation more strongly than the other compounds may be explained by its more prolonged effect on mTOR signaling (FIG. 2E), whereas MJX005 and MJX006 both only inhibited mTOR signaling transiently (FIGS. 2D & 2F).

Example 7: Anti-Aging Effect in Mouse Model

Figure 7:
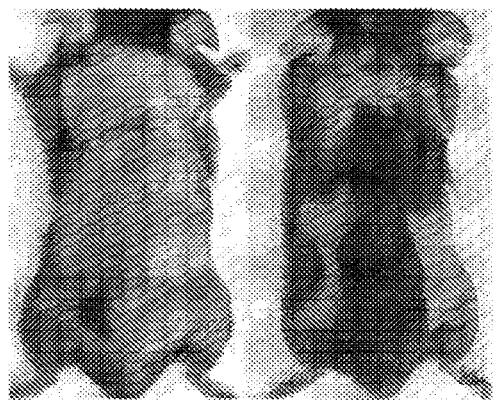
FIG. 7 shows the effect of an exemplary compound of the present invention on hair regrowth in mice.

The effects of the compounds on mouse models were evaluated. It is known that that α-KB prevents hair loss in old C57BL/6 mice as well as stimulates hair regrowth in mice. It was found that MJX002 similarly stimulates hair regrowth in 6 week old C57BL/6 mice. Mouse dorsal hair was shaved by trimmer on week 7 and MJX002 was dissolved in Transdermal Gel at 16 mM and applied on the dorsal skin every other day. Mice were monitored for the appearance of skin pigmentation, which signals the initiation of anagen. Treated mice showed accelerated pigmentation and hair growth after 40 days. (FIG. 7)

Example 8: Treatment of *C. elegans* with MJX006

N2 *C. elegans* lifespan was extended significantly by all three tested doses of MJX006. At the optimal dose of 2 mM, worms lived 24.2% longer than controls, which is comparable to the 24.6% lifespan extension achieved by 4 mM α-KB in this experiment. (FIG. 8)

TABLE 4

Figure 8:
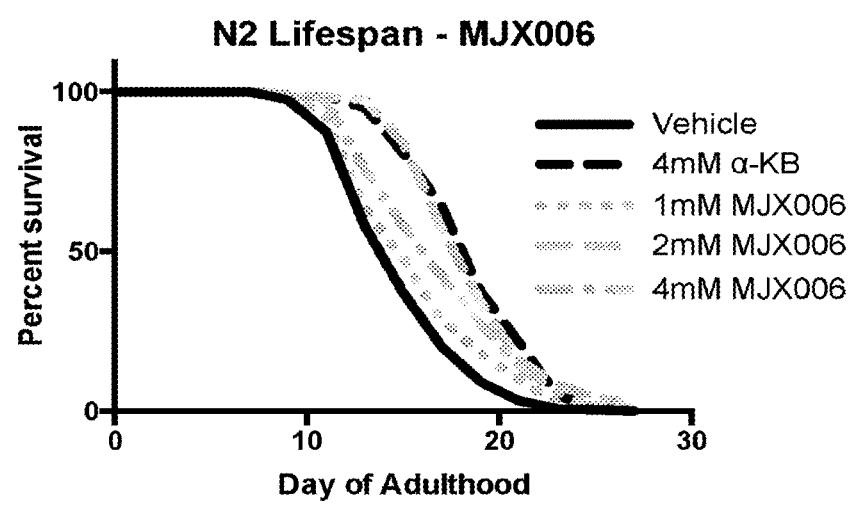
FIG. 8 shows the treatment of C. elegans with MJX006.

Data from FIG. 8

| | | Treatment: | | |
|---|---|---|---|---|
| | DMSO | 4 mM αKB | 1 mM MJX006 | 2 mM MJX006 | 4 mM MJX006 |
| mean lifespan | 15.3 | 19.1 | 16.2 | 19.0 | 17.4 |
| % increase | | 24.6 | 6.3 | 24.2 | 13.9 |
| p-value (Log-Rank) | | <0.0001 | 0.0366 | <0.0001 | <0.0001 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of Formula (VA), or a pharmaceutically acceptable salt thereof:

(VA)

or a compound of Formula (IVA), or a pharmaceutically acceptable salt thereof:

(IVA)

wherein
  each $R^4$ is independently selected from unsubstituted and substituted alkyl;
  each $R^6$ is alkyl;
  each $R^8$ is independently selected from H, unsubstituted and substituted alkyl; and
  wherein $R^4$ and $R^8$ are not substituted with an oxo group.

2. The compound of claim 1, wherein the compound has the structure of Formula (IVA), or a pharmaceutically acceptable salt thereof:

(IVA)

wherein
  each $R^6$ is alkyl;
  $R^4$ is unsubstituted or substituted alkyl; and
  $R^8$ is H, unsubstituted or substituted alkyl.

3. A compound of the structure of Formula (VA), or a pharmaceutically acceptable salt thereof:

(VA)

wherein $R^4$ and $R^8$ are unsubstituted or substituted alkyl.

4. A compound selected from:

(MJX003)

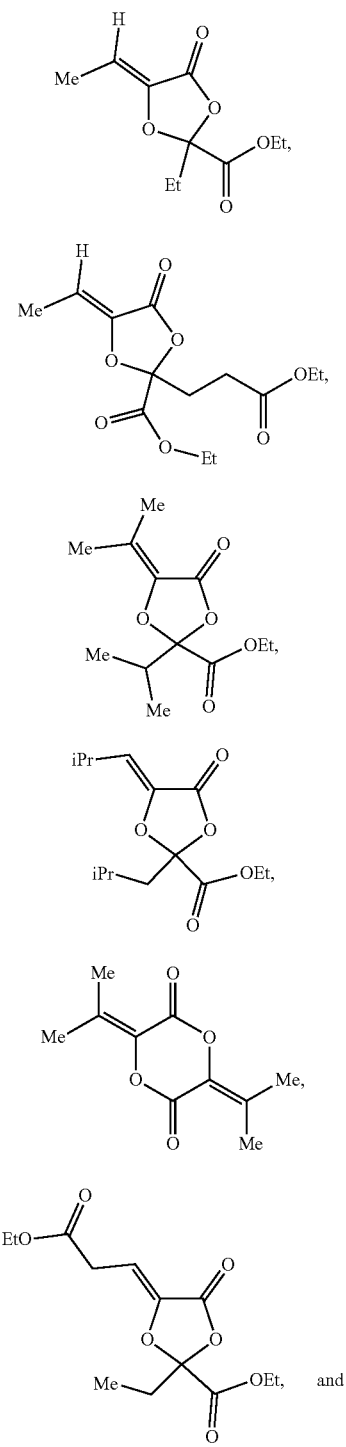

(MJX005)

(MJX006)

(MJX008)

(MJX010)

(MJX011)

(MJX012)

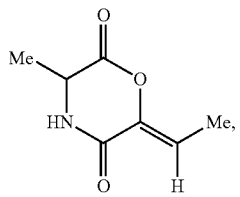

(MJX013)

or a pharmaceutically acceptable salt or thereof.

5. A pharmaceutical composition comprising a compound of claim 1, or a pharmaceutically acceptable salt thereof, and at least one pharmaceutically acceptable excipient.

6. The pharmaceutical composition of claim 5, wherein the pharmaceutical composition is formulated for administration to a mammal by intravenous administration, subcutaneous administration, oral administration, inhalation, nasal administration, dermal administration, or ophthalmic administration.

7. The pharmaceutical composition of claim 5, wherein the pharmaceutical composition is in the form of a tablet, a pill, a capsule, a liquid, a suspension, a gel, a dispersion, a solution, an emulsion, an ointment, or a lotion.

8. The compound of claim 3, wherein the compound is

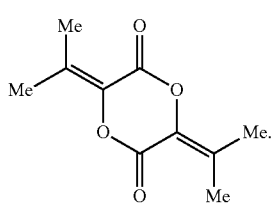

(MJX011)

9. A pharmaceutical composition comprising a compound of claim 3, or a pharmaceutically acceptable salt thereof, and at least one pharmaceutically acceptable excipient.

10. The pharmaceutical composition of claim 9, wherein the pharmaceutical composition is formulated for administration to a mammal by intravenous administration, subcutaneous administration, oral administration, inhalation, nasal administration, dermal administration, or ophthalmic administration.

11. The pharmaceutical composition of claim 9, wherein the pharmaceutical composition is in the form of a tablet, a pill, a capsule, a liquid, a suspension, a gel, a dispersion, a solution, an emulsion, an ointment, or a lotion.

12. The compound of claim 1, wherein $R^4$ and $R^8$ are optionally substituted with a halogen, a hydroxyl, an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

\* \* \* \* \*